US008158118B2

(12) United States Patent
Simmons et al.

(10) Patent No.: US 8,158,118 B2
(45) Date of Patent: *Apr. 17, 2012

(54) MESENCHYMAL PRECURSOR CELL

(75) Inventors: Paul Simmons, East Melbourne (AU); Andrew Zannettino, Adelaide (AU); Stan Gronthos, Bethesda, MD (US)

(73) Assignee: Angioblast Systems, Inc., New York, NY (US)

( * ) Notice: Subject to any disclaimer, the term of this patent is extended or adjusted under 35 U.S.C. 154(b) by 524 days.

This patent is subject to a terminal disclaimer.

(21) Appl. No.: 11/169,875

(22) Filed: Jun. 29, 2005

(65) Prior Publication Data

US 2005/0281790 A1  Dec. 22, 2005

Related U.S. Application Data

(62) Division of application No. 10/030,411, filed as application No. PCT/AU00/00822 on Jul. 7, 2000, now Pat. No. 7,122,178.

(30) Foreign Application Priority Data

Jul. 7, 1999 (AU) ..................... PQ 1477

(51) Int. Cl.
*A01N 63/00* (2006.01)
*A61K 35/26* (2006.01)
*C12N 5/08* (2006.01)
*C12N 5/00* (2006.01)

(52) U.S. Cl. ........ 424/93.1; 424/577; 435/325; 435/372

(58) Field of Classification Search ........................ None
See application file for complete search history.

(56) References Cited

U.S. PATENT DOCUMENTS

| | | | |
|---|---|---|---|
| 5,197,985 A | 3/1993 | Caplan et al. | |
| 5,226,914 A | 7/1993 | Caplan et al. | |
| 5,405,772 A | 4/1995 | Ponting et al. | |
| 5,486,359 A | 1/1996 | Caplan et al. | |
| 5,580,754 A | 12/1996 | Samal | |
| 5,591,625 A | 1/1997 | Gerson et al. | |
| 5,811,094 A | 9/1998 | Caplan | |
| 5,827,740 A | 10/1998 | Pittenger | |
| 5,837,539 A | 11/1998 | Caplan et al. | |
| 5,922,597 A | 7/1999 | Verfaillie et al. | |
| 5,980,887 A | 11/1999 | Isner et al. | |
| 6,022,540 A | 2/2000 | Bruder et al. | |
| 6,087,113 A | 7/2000 | Caplan et al. | |
| 6,261,549 B1 | 7/2001 | Fernandez et al. | |
| 6,322,784 B1 | 11/2001 | Pittenger et al. | |
| 6,335,195 B1 | 1/2002 | Rodgers et al. | |
| 6,387,367 B1 | 5/2002 | Davis-Sproul et al. | |
| 6,387,369 B1 | 5/2002 | Pittenger et al. | |
| 6,645,727 B2 | 11/2003 | Thomas et al. | |
| 6,709,864 B1 | 3/2004 | Pittenger et al. | |
| 7,122,178 B1 * | 10/2006 | Simmons et al. | 424/93.1 |
| 2002/0085996 A1 | 7/2002 | McIntosh et al. | |
| 2004/0107453 A1 | 6/2004 | Furcht et al. | |
| 2005/0019911 A1 | 1/2005 | Simmons et al. | |
| 2005/0158289 A1 | 7/2005 | Simmons et al. | |
| 2006/0008452 A1 | 1/2006 | Simmons et al. | |
| 2006/0193840 A1 | 8/2006 | Gronthos et al. | |
| 2006/0286077 A1 | 12/2006 | Gronthos et al. | |
| 2007/0065938 A1 | 3/2007 | Gronthos et al. | |
| 2007/0274958 A1 | 11/2007 | Shi et al. | |

FOREIGN PATENT DOCUMENTS

| | | |
|---|---|---|
| WO | WO 99/03973 A | 1/1999 |
| WO | WO 00/06701 | 2/2000 |
| WO | WO 01/04268 | 1/2001 |
| WO | WO 01/04268 A1 | 1/2001 |
| WO | WO 0111011 | 2/2001 |
| WO | WO 02/07679 | 1/2002 |
| WO | WO 2004/084921 A1 | 10/2004 |
| WO | WO 2004/085630 | 10/2004 |

OTHER PUBLICATIONS

Simmons, P.J., et al., "Isolation, Characterization and Functional Activity of Human Marrow Stromal Progenitors in Hemopoiesis," *Advances in Bone Marrow Purging and Processing: Fourth International Symposium*, 1994, pp. 271-280.
Gronthos, S., et al., "The STRO-1+ Fraction of Adult Human Bone Marrow Contains the Osteogenic Precursors," *Blood*, vol. 84, No. 12, 1994, pp. 4164-4173.
Doherty, M.J. et al. (1998) "Vascular Pericytes Express Osteogenic Potential In Vitro and In Vitro" *J. Bone and Mineral Research* 13, pp. 828-838.
Gronthos, S. et al. (2002) "Stem Cell Properties of Human Dental Pulp Stem Cells" *J. Dent. Res.* 81(8), pp. 531-535.
Jones, E.A. et al. (2002) "Isolation and Characterization of Bone Marrow Multipotential Mesenchymal Progenitor Cells" *Arthritis & Rheumatism* 46(12), pp. 3349-3360.
Shi, S. et al. (2001) "Comparison of Human Dental Pulp and Bone Marrow Stromal Stem Cells by cDNA Microarray Analysis" *Bone* 29(6), pp. 532-539.
Alberico et al (1987) Blood;69:1120.
Allen, T.D.: Haemopoietic microenvironment in vitro: Ultrastructural aspects. In Porter R. Whelan J (eds); "Microenvironments in haemopoietic and lymphoid differentiation." CIBA Foundation Symposium 84. London: Pitman Medical, 1981, pp. 38-67.
Allen et al (1990a) Immunol. Ser. 49:1.
Allen et al (1990b) Marrow Biology and Stem Cells. In Colony Stimulating Factors: Molecular and Cellular Biology, edited by T.M. Dexter, J.M. Garland and N.G. Testa: New York: Marcel Decker, 1990b. pp. 1-38.

(Continued)

*Primary Examiner* — Michail Belyavskyi
(74) *Attorney, Agent, or Firm* — John P. White; Cooper & Dunham LLP

(57) ABSTRACT

A method of enriching mesenchymal precursor sells including the step of enriching for cells based on at least two markers. The markers may be either i) the presence of markers specific for mesenchymal precursor cells, ii) the absence of markers specific for differentiated mesenchymal cells, or iii) expression levels of markers specific for mesenchymal precursor cells. The method may include a first solid phase sorting step utilizing MACS recognizing expression of the antigen to the STRO-1 Mab, followed by a second sorting step utilizing two color FACS to screen for the presence of high level STRO-1 antigen expression as well as the expression of VCAM-1.

14 Claims, 9 Drawing Sheets

OTHER PUBLICATIONS

Figure 1:
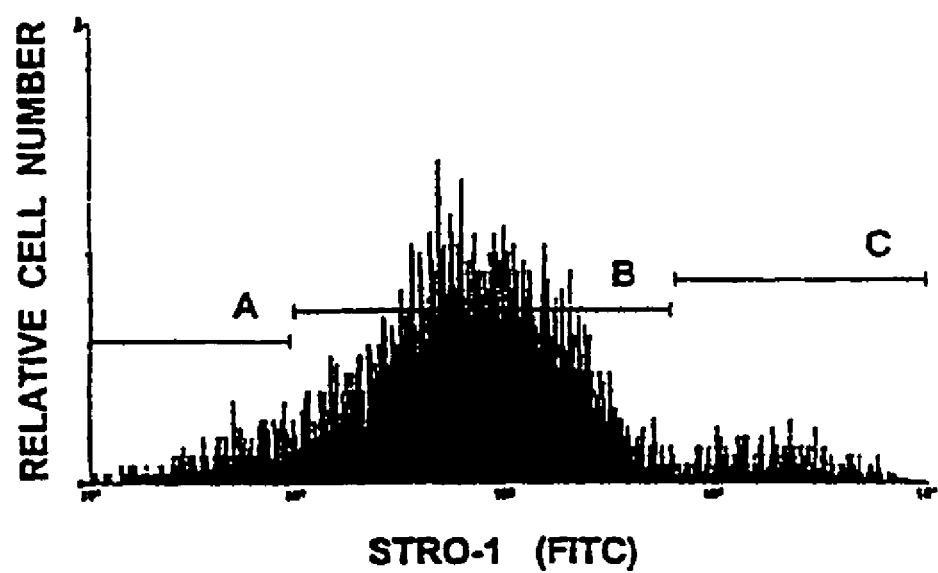

Anklesaria et al (1989) Blood. 74:1144.
Anklesaria et al (1987) Proc. Natl. Acad. Sci. USA. 84:7681.
Bennett et al (1991) Journal of Cell Science. 99:131.
Bentley (1982) Br J Haematol. 50:1.
Castro-Malaspina et al (1980) Blood. 56:289.
Castro-Malaspina et al. (1981) Blood. 57:781.
Dexter et al. (1977) J Cell Physiol. 91:335.
Dexter et al Kroc Foundation Series vol. 18; Alan R. Liss, Inc., New York; p. 57-96. 1984.
Fong et al (1997) BioTechniques. 23:1029.
Friedenstein (1976) International Review of Cytology. 47:327.
Friedenstein et al (1970) Cell Tissue Kinetics. 3:393.
Friedenstein et al. (1992) Bone and Mineral. 18:199.
Friedenstein (1980) "Stromal mechanisms of bone marrow: cloning in vitro and retransplantation in vivo." Immunology of Bone Marrow Transplantation; Ed: S. Thienfelder; Springer-Verlag Berlin; p. 19-29, 1980.
Gronthos et al. (1994) Blood. 84:4164.
Gronthos and Simmons (1995) Blood. 85:929.
Huang and Terstappen (1992) Nature. 360:745.
Keating et al. (1982) Nature. 298: 280.
Kim et al. (1994) Science, 266:2011.
Knopse et al. (1966) Blood. 28:398.
Knopse et al. (1972) Blood. 39:331.
Lichtman (1981) Experimental Hematology. 9:391.
Long (1992) Exp Hematol. 20:288.
MacManus and Weiss (1984) Blood. 64:1036.
McIntyre and Bjornson (1986) Exp Hematol. 14:833.
Miltenyi et al. (1990) Cytometry. 11:231.
Owen (1985) Bone and Mineral Research. 3:1.
Owen and Friedenstein (1988) CIBA Foundation symposium. 136:42.
Perkins and Fleischman (1990) Blood. 75:620.
Piersma et al. (1983) Br. J. Haematol. 54:285.
Rothstein et al. (1985) Blood. 65:744.
Simmons and Gronthos. (1991) International Journal of Cell Cloning. 9:408 [abstract].
Simmons et al.(1994) Advances in Bone Marrow Purging and Processing: Fourth International Symposium. Progress in Clinical Biological Research. 389:271.
Simmons et al. (1987) Nature 328:429.
Simmons and Torok-Storb (1991a) Blood. 78:55.
Simmons and Torok-Storb (1991b) Blood. 78:2848.
Tavassoli and Friedenstein (1983) Ann J Hematol. 15:195.
Tavassoli and Crosby (1968) Science. 161:54.
Testa et al. (1988) Long-term Bone Marrow Damage after Cytotoxic Treatment:Stem Cells and Microenvironment in Hematopoiesis: Long-term Effects of Chemotherapy and Radiation (Hematology/vol. 8), eds. Testa, N.G., Gale, R.P., Marcel Dekker, Inc. New York and Basel, 1988, pp. 75-92.
Van Vlasselaer et al (1994) Blood. 84:753.
Waller et al. (1995) Blood. 85:2422.
Weiss (1976) Anatomical Record. 186:161.
Clarke, Emer, "Mesenchymal Cells" www.stemcell.com (mini-review).
Hellstrom et al. (1999) Development 126, 2047.
Zoltowska, et al. (2001) Arch Immunol Ther Exp (Warsz) 49:59-61.
Shi S et al: "Perivascular niche of postnatal mesenchymal stem cells in human bone marrow and dental pulp." Journal of Bone and Mineral Research, vol. 17, No. Suppl 1, Sep. 2002, p. S446, XP009083412 & Twenty-Fourth Annual meeting of the American Society for Bone and Mineral Research; San Antonio, Texas, USA; Sep. 20-24, 2002.
Gronthos S et al: "Postnatal human dental pulp stem cells (DPSCs) in vitro and in vivo." Proceedings of the National Academy of Sciences of USA, National Academy of Science, Washington, DC, US, vol. 97, No. 25, Dec. 5, 2000, pp. 13625-13630.
Shi S et al: "Perivascular niche of postnatal mesenchymal stem cells in human bone marrow and dental pulp." Journal of Bone and Mineral Research, New York, NY, US, vol. 18, No. 4, Apr. 2003, p. 696-704.
Tse H F et al: "Angiogenesis in ischaemic myocardium by intramyocardial autologous bone marrow mononuclear cell implantation." Lancet The, Lancet Limited, London, GB, vol. 361, No. 9351, Jan. 4, 2003, pp. 47-49.
Zvaifler, et al., (2000) "Mesenchymal precursor cells in the blood of normal individuals," Arthritis Research and Therapy, 2: 477-488.
Ji, et al., (2004) "Interactions of Chemokines and Chemokine Receptors Mediate the Migration of Mesenchymal Stem Cells to the Impaired Site in the Brain After Hypoglossal Nerve Injury," Stem Cells, 22: 415-427.
Sordi, et al., (2005) "Bone marrow mesenchymal stem cells express a restricted set of functionally active chemokine receptors capable of promoting migration to pancreatic islets," Blood, 106(2): 419-427.
Wynn, et al., (2004) "A small proportion of mesenchymal stem cells strongly expresses functionally active CXCR4 receptor capable of promoting migration to bone marrow," Blood, 104(9): 2643-2645.
Kortesidis, et al., (2005) "Stromal-derived factor-1 promotes the growth, survival, and development of human bone marrow stromal stem cells," Blood, 105(10): 3793-3801.
Gronthos, S., et al., (1999) "Differential Cell Surface Expression of the STRO-1 and Alkaline Phosphatase Antigens on Discrete Developmental Stages in Primary Culture of Human Bone Cells," Journal of Bone and Mineral Research, 14(1): 47-56.
Stewart, K., et al., (1999) "Further Characterization of Cells Expressing STRO-1 In Cultures of Adult Human Bone Marrow Stromal Cells," Journal of Bone and Mineral Research, 14(8): 1345-1356.
Cochlovius, B. et al. (2003) "Therapeutic Antibodies," Modern Drug Discovery pp. 33-34, 37-38.
Hansson, M. et al. (2007) "Commentary: Isolated Stem Cells-Patentable as Cultural Artifacts?" V.25, pp. 1507-1510.
Gronthos et al. Journal of Hematotherapy, 1996. 5, 15-23.
Supplementary European Search Report from European Patent Office, Application No. EP 04 72 3935, May 10, 2007.
Supplementary European Search Report from European Patent Office, Application No. EP 04 72 3937, May 25, 2007.
International Search Report issued by the International Searching Authority (ISA/AU) on May 17, 2004 in connection with International Application No. PCT/AU2004/000416.
International Preliminary Report on Patentability issued May 17, 2004 in connection with International Application No. PCT/AU2004/000416.
International Search Report issued by the International Searching Authority (ISA/AU) on May 17, 2004 in connection with International Application No. PCT/AU2004/000417.
International Preliminary Report on Patentability issued by the International Bureau of WIPO on Oct. 1, 2005 in connection with International Application No. PCT/AU2004/000417.
International Search Report issued by the International Searching Authority (ISA/AU) on Aug. 22, 2005 in connection with International Application No. PCT/AU2005/000953.
International Search Report issued by the International Searching Authority (ISA/AU) on Nov. 25, 2005 in connection with International Application No. PCT/AU2005/001445.
U.S. Appl. No. 11/663,570, filed Mar. 23, 2007.
U.S. Appl. No. 11/663,563, filed Mar. 23, 2007.
Axelrad et al., New Technologies for the Enhancement of Skeletal Repair, Injury, Int. J. Care Injured (2007) 38S1:S49-S62.
Bruder et al., Mesenchymal Stem Cells in Bone Development, Bone Repair, and Skeletal Regeneration Therapy, J. Cell Biochem; (1994) 56:283-294.
Dennis et al., Osteogenesis in Marrow-Derived Mesenchymal Cell Porous Ceramic Composites Transplanted Subcutaneously: Effect of Fibronectin and Laminin on Cell Retention and Rate of Osteogenic Expression, Cell Transplant (1992) 1:23-32, Abstract.
Barry, F.P. (2003) "Biology and Clinical Applications of Mesenchymal Stem Cells." Birth Defect Research (Part C) 69:250-256.
Cassiede, P. et al. (1996) "Osteochondrogenic Potential of Marrow Mesenchymal Progenitor Cells Exposed to . . . " Journal of Bone and Mineral Research vol. 11(9):1264-1273.
Chopp, M. and Li, Y. (2002) "Treatment of Neural Injury with Marrow Stromal Cells." The Lancet Neurology 1:92-100.

Dennis JE, et al. (2002), The STRO-1+ Marrow Cell Population is Multipotential, Cells Tissues Organs, 170:73-82.

Greenberger, J. and Keating, A. (1996) "The Hematopoietic Effects Microenvironment." Keystone Symposium, Taos, New Mexico14:366-367.

Finney, M.R. et al. (2006) Direct Comparison of Umbilical Cord Blood versus Bone Marrow-Derived Endothelial Precursor Cells in . . . Biol. Blood and Marrow Transplant 12:585-593.

Hoerstrup SP et al. (2002), Tissue Engineering of Functional Trileaflet Heart Valves From Human Marrow Stromal Cells, Circulation 106(Suppl):I-143-I150.

Kassem, M. (2004) "Mesenchymal Stem Cells: Biological Characteristics and Potential Clinical Applications." Cloning Stem Cells 6:369-374.

Kang Yong Jung et al. (2004) "Involvement of PI-3-kinase, JNK, PKC, and PKA in the PDGF-induced proliferation in human adipose tissue-derived . . ." vol. 18(8) C253.

Le Blanc, K. and Ringden, O. (2005) "Immunobiology of Human Mesenchymal Stem Cells and Future Use in Hematopoietic . . ." Biology of Blood and Marrow Transplantation 11:321-334.

Murray et al. (1996) "Fetal Bone Marrow CD34+CD41+ Cells are Enriched for Multipotent Hematopoietic Progenitors, but not for Pluripotent Stem Cells." Exp. Hematol. 24:236-245.

Pan, Beiqing et al. (2004) "The nitrogen-containing bisphosphonate, zaledronic acid, increases mineralisation of human bone-derived cells in vitro." Bone 34:112-123.

Summer, R. and Fine, A. (2008) "Mesenchymal Progenitor Limitations and Recommendations." Proc.Am, Thorac. Soc 5:707-710.

International Preliminary Report . . . issued by the International Bureau of WIPO on Oct. 1, 2005 in connection with International Application No. PCT/AU2004/000416.

Extended European Search Report issued Dec. 27, 2007 in connection with European Application No. 05787106.3.

Supplementary European Search Report issued Jan. 2, 2008 in connection with European Application No. 05754008.0.

Apr. 4, 2008 Restriction Requirement issued in connection with U.S. Appl. No. 10/551,326.

Sep. 12, 2008 Office Action issued in connection with U.S. Appl. No. 10/551,162.

Oct. 16, 2008 Office Action issued in connection with U.S. Appl. No. 10/955,709.

Nov. 13, 2008 Office Action issued in connection with U.S. Appl. No. 10/551,326.

Nov. 17, 2008 Office Action issued in connection with U.S. Appl. No. 11/326,736.

European Examination Report issued Feb. 27, 2009 in connection with European Application No. 04723937.1.

Apr. 28, 2009 Final Office Action issued in connection with U.S. Appl. No. 10/813,747.

Holden et al. (2002), "Plasticity Time for A Reappraisal?" Science 296:2126-2129.

Poulsom et al. (2003), "Bone Marrow Stem Cells Contribute to Healing of the Kidney," J. Am. Soc. Nephrol. 14:s48-s54.

Yang XV, et al. (2006), "Evaluation of Human Bone Marrow Stromal Cell Growth on Biodegradable . . ." Biochemical and Biophysical Research Communications 342:1098-1107.

Fujii, S. et al. (2008), "Investigating a Clonal Human Periodontal Ligament Progenitor/Stem Cell Line In Vitro and In Vivo," J. Cell. Physiol. 215:743-749.

Bianco, P. et al. (2001), "Bone Marrow Stromal Stem Cells: Nature, Biology, and Potential Applications," Stem Cells 19:180-192.

Neuhaus T. et al. (2003) "Stromal cell-derived factor 1alpha (SDF-1alpha) induces gene-expression of early growth response-1 . . ." Cell Proliferation. 36:75-86.

Salcedo R. et al. (1999) "Vascular endothelial growth factor and basic fibroblast growth factor induce expression of CXCR4 . . ." American Journal of Pathology. 154:1125-1135.

Kanbe K. et al. (2002) "Stimulation of Matrix Matalloprotease 3 Release from Human Chondrocytes by the Interaction of Stromal Cell-Derived . . ." Arthritis & Rheumatism 46:130-137.

Final Office Action issued Jun. 22, 2009 in connection with U.S. Appl. No. 10/551,162.

Final Office Action issued Jul. 16, 2009 in connection with U.S. Appl. No. 10/955,709.

Final Office Action issued Sep. 29, 2009 in connection with U.S. Appl. No. 10/551,326.

Final Office Action issued Oct. 8, 2009 in connection with U.S. Appl. No. 11/326,736.

Oct. 29, 2009 Notice of Allowance issued in connection with U.S. Appl. No. 10/813,747.

Examination report issued Oct. 10, 2009 in connection with European Application No. 05754008.0.

Office Action issued Jan. 19, 2010 in connection with corresponding Japanese Application No. 2006-503989.

Office Action issued Mar. 16 2010 in connection with U.S. Appl. No. 11/663,570.

Al-khaldi et al. (2003) "Therapeutic Angiogenesis Using Autologous Bone Marrow Stromal Cells: Improved Blood Flow in a Chronic Limb Ischemia Model" Ann Thorac Surg 75:204-209.

Kocher et al. (2001) "Neovascularization of Ischemic Myocardium by Human Bone-Marrow-Derived Angioblasts Prevents Cardiomyocyte Apoptosis, Reduces Remodeling and Improves Cardiac Function" Nature Medicine 7:430-436.

Reyes et al. (2002) "Origin of Endothelial Progenitors in Human Postnatal Bone Marrow" Clin. Invest. 109:337-346.

Office Action issued Nov. 8, 2010 in connection with U.S. Appl. No. 12/660,003.

Office Action issued Jan. 24, 2011 in connection with U.S. Appl. No. 12/660,003.

Office Action Issued Aug. 26, 2010 in connection with U.S. Appl. No. 10/551,162.

Notice of Allowance issue Jan. 14, 2011 in connection with U.S. Appl. No. 10/551,162.

Office Action issued Jan. 19, 2011 in connection with U.S. Appl. No. 10/551,326.

Office Action issued May 24, 2011 in connection with U.S. Appl. No. 11/326,736.

Office Action issued Sep. 22, 2009 in connection with U.S. Appl. No. 11/663,570.

Communication Pursuant to Art. 94(3) EPC issued Apr. 16, 2010 in connection with European Application No. 05787106.3.

Communication Pursuant to Art. 94(3) EPC issued Dec. 16, 2010 in connection with European Application No. 05787106.3.

* cited by examiner

SEQUENCE LISTING

```
<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 1
aatccgtcga gcagagtt                                                  18

<210> SEQ ID NO 2
<211> LENGTH: 26
```

```
<212> TYPE: DNA
<213> ORGANISM: Artificial Sequence
<220> FEATURE:
<223> OTHER INFORMATION: Oligonucletide primer

<400> SEQUENCE: 2
gtgcccttcc cttaccctta ccctaa                                              26
```

MESENCHYMAL PRECURSOR CELL

This application is a divisional of U.S. Ser. No. 10/030,411, filed Apr. 11, 2002, now U.S. Pat. No. 7,122,178, issued Oct. 17, 2006, a §371 national stage of PCT International Application No. PCT/AU00/00822, filed Jul. 7, 2000, which claims priority of Australian Patent Application No. PQ 1477, filed Jul. 7, 1999, now abandoned, the contents of which are hereby incorporated by reference.

This invention relates to the enrichment of mesenchymal precursor cells using a combination of cell surface markers, and to a cell population of mesenchymal precursor cells.

Mesenchymal cells are derived from a number of tissues and act as the supportive structure for other cell types. Bone marrow for instance is made of both haematopoietic and mesenchymal derived cells. The mesenchymal cells include endothelial cells that form the sinuses and advetitial reticular cells that have characteristics consistent with adipocytes, fibroblasts and muscle cells.

It is believed that certain mesenchymal precursor cells (MPCs) are responsible for the formation of mesenchymal cells. In the bone MPCs are the formative pluripotent blast cells that are believed to be capable of differentiating into any of the specific types of connective tissues (i.e. the tissue of the body that support the specialised elements, particularly adipose, areolar, osseous, cartilaginous, elastic and fibrous connective tissues) depending upon the various environmental influences.

Purification or at least enrichment of MPCs is desirable for a variety of therapeutic reasons. The reasons include regeneration of missing or damaged skeletal tissue, enhancing the implantation of various plastic or metal prosthetic devices through the attachment of the isolated and culturally expanded marrow derived mesenchymal cells onto the porous surfaces of the prosthetic devices, which upon activation and subsequent differentiation of marrow-derived mesenchymal cells produce natural osseous bridges.

Composite grafts of cultured mesenchymal cells might be used to augment the rate of haematopoietic cell reserve during bone marrow transplantation.

A class of defects that may be repaired by cultured marrow-derived mesenchymal cells expanded from the MPCs of the present invention is the class of large skeletal defects in bone caused by injury or produced by the removal of large sections of bone infected with tumour. Under normal circumstances this type of defect does not heal and creates nonunion of the bone. This type of defect may be treated by implanting cultured mesenchymal cells contained in calcium phosphate ceramic vehicles into the defect site.

A second class of defect that may be repaired by cultured marrow-derived mesenchymal cells expanded from the MPCs of the present invention, is the damaged articular cartilage generated by trauma or by diseases such as osteoarthritis and rheumatoid arthritis. Under normal circumstances, damage to articular cartilage does not heal except in very young individuals where the underlying bone is also damaged so that a bloody wound is created. It is projected by the present invention that this type of defect can be treated by implanting cultured marrow derived mesenchymal cells into the defect. The cells will be formatted in carriers which will hold the cells in the defect and present them in a manner (round cell morphology) that they differentiate into chondrocytes.

It is not clearly understood why composite grafts of cultured mesenchymal cells and ceramic induce recruitment of haematopoietic stem cells and other marrow elements, however, the fact that this does occur allows for the use of these grafts in a way to sequester haemopoietic stem cells and generate a haematopoietic stem cell reservoir. The reservoir of haematopoietic stem cells can then be used in clinical applications such as marrow transplantation as an alternative method for harvesting haematopoietic stem cells.

Another potential use for purified cells is as a means of gene therapy, by the introduction of exogenous nucleic acids for the expression of therapeutic substances in the bone marrow—see U.S. Pat. No. 5,591,625 by Gerson et al.

A purified source of MPCs is desirable for a number of reasons. One major reason is that if there is a mixed population, MPCs will respond to signals elicited by other cells to behave in a manner that might not be desired. Thus, for example, a contaminating cell might express a cytokine that evokes differentiation into adipose tissue, whereas one may require the cells for bone formation, in which case the usefulness of the MPCs is somewhat limited. Additionally for a reason similar to that given above, purified progenitor cells tend to be easier to handle and manage than less purified cells.

There have been many attempts at purifying or significantly enriching MPCs, however significant enrichment has until the present invention not been achieved. In contrast to the haemopoietic system, in which stem cells can be physically separated based upon differences in their expression of cell surface markers, the cell surface antigenic phenotype of MPCs remains relatively poorly defined. A further problem of purification of MPCs is a result of the physical association between mesenchymal cells and other cell types.

The bone and bone marrow (BM) tissues contain a phenotypically diverse population of stromal cell lineages that are currently thought to arise from a rare and primitive population of multi-potential mesenchymal precursor cells (MPC) [Owen, 1985; Owen and Friedenstein, 1988]. Bone marrow MPC can be readily measured by their ability to form adherent clonogenic clusters composed of fibroblastic-like cells (CFU-F: colony-forming-unit-fibroblast) in short-term liquid culture [Friedenstein et al, 1970; Castro-Malaspina et al, 1980]. In vitro studies have documented variations in the morphology and proliferative capacity of different BM MPC clones [Friedenstein et al, 1970; 1976; Castro-Malaspina et al, 1980; Owen et al, 1987; Bennett et al, 1991; Simmons and Gronthos, 1991]. The heterogeneous nature of the BM MPC population was further demonstrated in studies where culture expanded MPC clones displayed different developmental potentials in the presence of glucocorticoids or when transferred into ectopic sites in vivo [Friedenstein et al, 1980; Owen et al, 1987; Bennett et al, 1991]. Collectively, these studies support the concept of a stromal cell hierarchy of cellular differentiation by analogy with the haemopoietic system.

Given the extensive literature regarding the characterisation of haemopoietic stem cells and their progeny there has been little progress towards the identification of the various elements which constitute the bone marrow stromal precursor compartment. This is due in part to the low incidence of MPC in aspirates of marrow (0.05% to 0.001%) [Castro-Malaspina et al 1980; Simmons and Torok-Storb, 1991a; 1991b; Falla et al, 1993; Waller et al, 1995a], and because of the paucity of antibody reagents that allow for the precise identification and isolation of the MPC population. Stromal precursor cells have been partially enriched from bone marrow aspirates through their binding to different lectins such as soya bean agglutinin and wheat germ agglutinin or by using a negative immunoselection process based on their lack of expression of various cell surface antigens restricted to the myeloid, erythroid and lymphoid cell lineages [Simmons and Torok-Storb 1991a; 1991b; Simmons et al, 1994; Rickard et al, 1996]. However, the inefficiency of these selection strategies has resulted in the presence of contaminating populations of accessory cells and haemopoietic progenitor cells. Moreover, a major difficulty in using techniques such as fluorescense activated cell sorting (FACS) to positively select for pure populations of MPC is that they share many common antigens with HSC including early developmental markers such as the human CD34 antigen and the murine stem cell antigen-1.

Recent advances in the study of human stromal stem cell biology have been attributed to the development of novel monoclonal antibodies (Mabs) which recognise antigens on BM MPC that are correspondingly not reactive with haemopoietic progenitors. We have previously described a monoclonal antibody, STRO-1 which identifies an as yet unidentified 60 kDa cell surface antigen expressed on all assayable MPC in aspirates of adult human BM [Simmons and Torok-Storb, 1991a]. The majority of the STRO-1$^+$ bone marrow mononuclear cells (BMMNC) (approximately 90%) have been identified as late stage glycophorin A$^+$ erythroblasts. The MPC population are restricted to the minor population of STRO-1$^+$ cells which lack glycophorin A [Simmons and Torok-Strob, 1991a]. Importantly, STRO-1 demonstrates no detectable binding to haemopoietic progenitors (CFU-GM, BFU-E, BFU-Meg, CFU-GEMM) nor to their precursors (pre-CFU) [Simmons and Torok-Storb, 1991a; Gronthos and Simmons, unpublished observations].

A systematic examination of the immunophenotype of MPC derived from adult human BM has previously been performed using two-color FACS analysis [Simmons et al, 1994]. A number of antigens were shown to be coexpressed with STRO-1 by essentially all BM MPC. These included the endopeptidases CD10 and CD13 and the adhesion molecules Thy-1 (CDw90), VCAM-1 (CD 106) and various members of the β1 (CD29) integrin family [Sirnmons et al, 1994]. This is in accord with the data of Terstappen and colleagues regarding the antigenic phenotype of human foetal BM MPC [Waller et al, 1995].

SUMMARY OF THE INVENTION

This invention arises from the finding that enrichment of mesenchymal precursor cells is greatly enhanced by the use of two markers specific for mesenchymal cells, that can be used to recognise early cells. To this end it will be appreciated that MPCs are early cells that are substantially at a pre-expansion stage of development and hence are precursors to mesenchymal stem cells in which a significant number of the population have expanded and are therefore incapable of further expansion. Thus, MPCs are cells that have yet to differentiate to fully committed mesenchymal cells. These cells need not however be stem cells in a strict sense, in that they are necessarily able to differentiate into all types of mesenchymal cells. There is a benefit in having an enriched pool of MPCs that are able to differentiate into bone forming cells only, in that these precursor cells have a greater proliferation potential. In particular in accordance with the present invention because the proportions of MPCs in the harvested population is large, the extent to which the population can be expanded is greatly enhanced.

The present invention provides an enrichment several orders of magnitude better than the best method known to the inventors before the present invention. The inventors have shown that an enriched population in which up to 50% of the MPCs can form colonies of ten or more cells can be achieved using the present invention. In contrast, the citations indicate that the best method known up until now has only achieved an enrichment of up to 0.01% cells capable of forming colonies.

It is to be noted that as discussed herein the presence of MPCs is based upon their colonigenic capacity, as determined by the presence of colonies of ten or more cells in liquid culture seeded with single cells after having been grown for 14 days.

In a broad form of a first aspect the invention could be said to reside in a method of enriching mesenchymal precursor cells (MPCs) the method including the steps of enriching for cells based on at least two markers, said markers being either the presence of, or expression levels of markers specific for mesenchymal precursor cells on the one hand, or absence of marker or levels of expression specific for differentiated mesenchymal cells on the other hand.

The preferred source of material for enrichment is bone marrow, and thus in a one form the method is limited to the enrichment of bone marrow derived mesenchymal stem cells. It is also likely that the method of this first aspect of the invention might be used to enrich stromal stem cells from other sources such as blood, epidermis and hair follicles. It is proposed that mesenchymal precursor cells isolated from, for example, skin should have the same potential as those cells isolated from bone marrow. An advantage in isolating cells from skin is that the harvesting is far less invasive than the harvesting of a sample of bone marrow.

It is anticipated that a proportion of the population purified will be stem cells, however, it is not yet known how to separate these stem cells from the MPC population. It has been observed however that a subpopulation has a much greater capacity to divide than others, and perhaps this subpopulation represents the stem cells. It is estimated that approximately 10 to 20% of the MPCs isolated by the illustrated Method of this invention are stem cells.

It is preferred that a significant proportion of the MPCs are capable of differentiation into at least two committed cell types selected from the group including but not limited to adipose, areolar, osseous, cartilaginous, elastic and fibrous connective.

It has been found that it is possible to purify MPCs by the above method to a degree where these cells are present in a purified population of which 50% of the MPCs can form colonies of ten or more cells. Therefore the method may result in a cell population in which at least 1% of the cells are MPCs that are colony forming, preferably at least 5% of the cells are MPCs that are colony forming, more preferably at least 10% of the cells are MPCs that are colony forming, and most preferably at least 40% of the cells are MPCs that are colony forming.

The nearest known purification is that by Pittenger et al. (Science 284; 143-147) where cells had been enriched using a Percoll gradient. These workers were only able to get colony forming units from 0.001-0.01% of cells. The present technique therefore results in a very significant enrichment when compared to these attempts.

The present invention is also to be contrasted to the enriched populations described by Caplan et al. in U.S. Pat. No. 5,837,539 who describes a method for the isolation, purification and culture expansion of mesenchymal stem cells which is said to give compositions having greater than 95% human mesenchymal stem cells. It is to be noted that the figure of 95% relates to populations of expanded mesenchymal stem cells, and is likely to reflect a lower number of colony forming units because the cells are at least partially expanded. Thus, Caplan starts with a population of BM cells comprising about 1 in 1000 MPCs and expands the population and then purifies the at least partially expanded population. In contrast the present invention can result in a population of about 1 in 2 cells that are able to form colonies of at least 10 MSCs.

Preferably the method includes enriching by selecting for the positive expression of at least one marker and more preferably both markers are selected for positive expression. These markers are most conveniently cell surface markers. The markers might be selected from a group of surface markers specific for MPC including but not limited to LFA-3, THY-1, VCAM-1, ICAM-1, PECAM-1, P-selectin, L-selectin, CD49b/CD29, CD49c/CD29, CD49d/CD29, CD29, CD18, CD61, 6-19, thrombomodulin, CD10, CD13, SCF, and the antigen recognised by STRO-1.

The marker might be absence of various surface markers indicative of commitment, such as CBFA-1, collagen type II, PPARγ2, glycophorin A.

In one preferred form at least one of the markers is the antigen recognised by STRO-1, and in particular the high level of expression of that antigen.

In another preferred form at least one of the markers is VCAM-1.

In one very specific form the two markers are the antigen recognised by STRO-1 and VCAM-1.

The specificity of the markers used in this process is not absolute. Thus even the most preferred markers occur on cell types other than mesenchymal cells, however their expression on the cell surfaces of other cell types is limited.

It will be understood that recognition of cells carrying the cell surface markers that form the basis of the separation can be effected by a number of different methods, however, all of these methods rely upon binding a binding agent to the marker concerned followed by a separation of those that exhibit binding, being either high level binding, or low level binding or no binding. The most convenient binding agents are antibodies or antibody based molecules, preferably being monoclonal antibodies or based on monoclonal antibodies because of the specificity of these latter agents. Antibodies can be used for both steps, however other agents might also be used, thus ligands for these markers may also be employed to enrich for cells carrying them, or lacking them.

The antibodies may be attached to a solid support to allow for a crude separation. The separation techniques should maximise the retention of viability of the fraction to be collected. Various techniques of different efficacy may be employed to obtain relatively crude separations. The particular technique employed will depend upon efficiency of separation, associated cytotoxicity, ease and speed of performance, and necessity for sophisticated equipment and/or technical skill. Procedures for separation may include, but are not limited to, magnetic separation, using antibody-coated magnetic beads, affinity chromatography and "panning" with antibody attached to a solid matrix. Techniques providing accurate separation include but are not limited to FACS.

The method might include the step of making a first partially enriched pool of cells by enriching for the expression of a first of the markers, and then the step of enriching for expression of the second of the markers from the partially enriched pool of cells.

It is preferred that the method comprises a first step being a solid phase sorting step, based on recognition of one or more of the markers. The solid phase sorting step of the illustrated embodiment utilises MACS recognising high level expression of STRO-1. This then gives an enriched pool with greater numbers of cells than if a high accuracy sort was used as a first step. If for example FACS is used first, many of the MPCs are rejected because of their association with other cells. A second sorting step can then follow using an accurate separation method. This second sorting step might involve the use of two or more markers. Thus in the illustrated embodiment two colour FACS is used to recognise high level expression of the antigen recognised by STRO-1 as wells as the expression of VCAM-1. The windows used for sorting in the second step can be more advantageously adjusted because the starting population is already partially enriched.

It will be understood that the invention is not limited to the enrichment of cells by their expression of only two markers and it may be preferred to enrich based on the expression of three or more markers.

The method might also include the harvesting of a source of the stem cells before the first enrichment step, which in the most preferred source comprises the step of harvesting bone marrow cells, using known techniques.

The preferred source of such cells is human, however, it is expected that the invention is also applicable to animals, and these might include domestic animals or animals that might be used for sport.

In a broad form of a second aspect the invention could be said to reside in an enriched population of mesenchymal precursor cells as purified by a method according to the first aspect of the invention.

It has been found that it is possible to purify MPCs to a degree where the purified population contains 50% of these cells that are capable of forming colonies of 10 or more cells.

In a broad form of a third aspect the invention could also be said to reside in a cell population in which at least 1% of the cells are MPCs that are colony forming, preferably at least 5% of the cells are MPCs that are colony forming, more preferably at least 10% of the cells are MPCs that are colony forming, and most preferably at least 40% of the cells are MPCs that are colony forming.

The cells of the enriched population preferably carry at least two markers selected from a group of surface markers specific for mesenchymal precursor cells including LFA-3, THY-1, antigen identified by STRO-1, VCAM-1, ICAM-1, PECAM-1, P-selectin, L-selectin, CD49b/CD29, CD49c/CD29, CD49d/CD29, CD29, CD18, CD61, 6-19, thrombomodulin, CD10, CD13 and SCF. Most preferably the cells carry the antigen identified by STRO-1 and VCAM-1.

It will also be understood that in a fourth aspect the invention encompasses a composition including the purified MPCs or a composition made from the purified MPCs.

The purified population of the second or third aspects of the invention, or the composition of the fourth aspect of the invention might be used in the formation and repair of bones, and as such a combination of MPCs as well as a suitable support may be introduced into a site requiring bone formation. Thus, for example, skeletal defects caused by bone injury or the removal of sections of bone infected with tumour may be repaired by implanting cultured MSCs contained in calcium phosphate ceramic vehicles into the defect site. For appropriate methods and techniques see Caplan et aL in U.S. Pat. No. 5,226,914 and U.S. Pat. No. 5,837,539, both of which use cruder preparations of stem cells.

In addition, the enriched population or composition may be used to assist in anchoring prosthetic devices. Thus, the surface of a prosthetic device such as those used in hip, knee and shoulder replacement, may be coated with the enriched MPCs prior to implantation. The MPCs may then differentiate into osteogenic cells to thereby speed up the process of bony ingrowth and incorporation of the prosthetic device (see Caplan et al. in U.S. Pat. No. 5,226,914 and U.S. Pat. No. 5,837,539).

The enriched population or composition mnight also be used in gene therapy so that, for example, an enriched population may have exogenous nucleic acid transformed into it and then such a population may be introduced into the body of the patient to treat a disease or condition. Alternatively it might be used for the release of therapeutics. For appropriate techniques we refer to U.S. Pat. No. 5,591,625 by Gerson et al. which uses cruder preparations of stem cells.

Alternatively the enriched population or composition may be used to augment bone marrow transplantation, wherein the composition containing purified MSCs can be injected into a patient undergoing marrow transplantation prior to the introduction of the whole marrow. In this way the rate of haemopoiesis may be increased, particularly following radiation or chemotherapy. The composition might also encompass a mixture of MPCs and haemopoietic cells which may be useful in radiotherapy or chemotherapy.

FIGURE LEGENDS

FIG. 1 The frequency histogram represents the immunofluorescence analysis by FACS of BMMNC isolated by MACS on the basis of STRO-1 (FITC) expression: STRO-$1^{dull}$ cell fraction (A); STRO-$1^{intermediate}$ cell fraction (B); STRO-$1^{bright}$ cell fraction (C); The histogram is based on $10^4$ events collected as list mode data.

Figure 2:
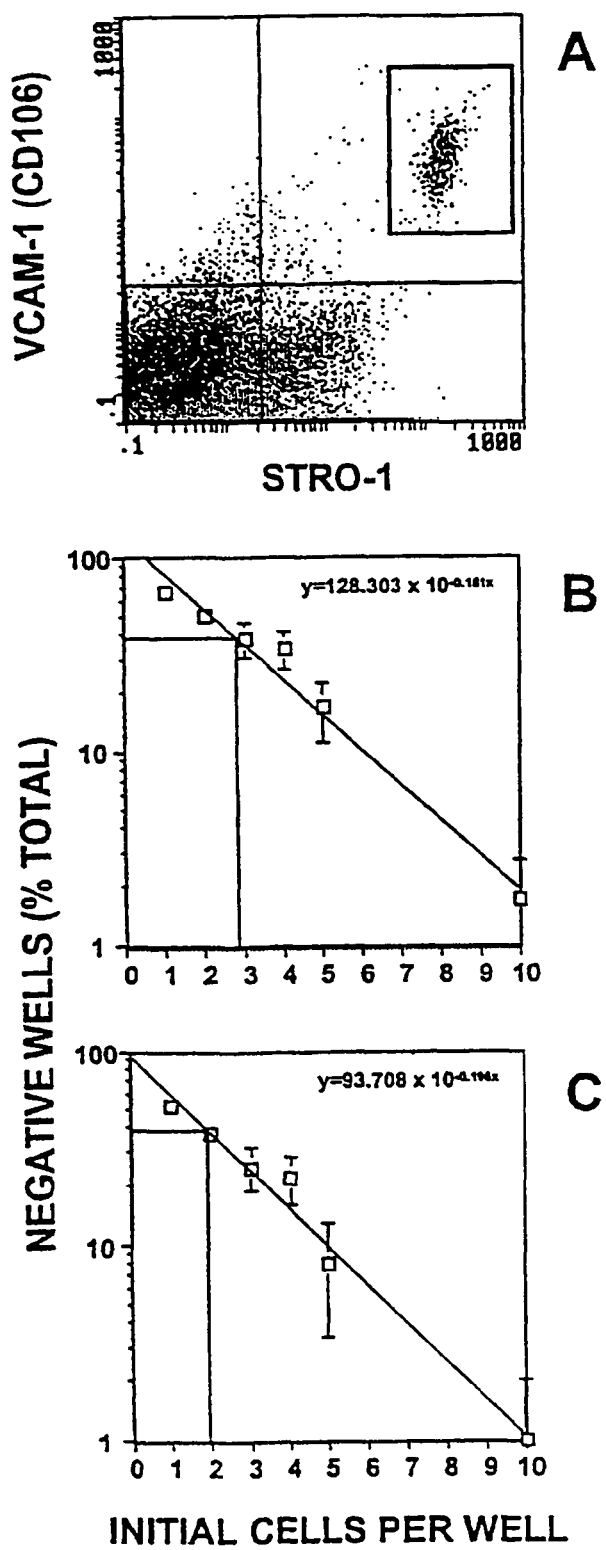

FIG. 2 Dual-colour flow cytometric analysis of VCAM-1 (PE) expression by STRO-$1^+$ (FITC) BMMNC isolated by MACS. The dot plot histogram represents $5 \times 10^4$ events collected as listmode data STRO-$1^{bright}$/VCAM-$1^+$ cells were sorted by FACS (rectangle), which represented approximately 0.1% of the total BMMNC population (A). The incidence of clonogenic cells (B) colonies (>50 cells) and (C) colonies+clusters (>10<50 cells) based on STRO-$1^{bright}$/VCAM-$1^+$ expression. The frequency of clonogenic cells was determined by limiting dilution analysis (24 replicates per cell concentration) employing Poisson distribution analysis.

Figure 3:
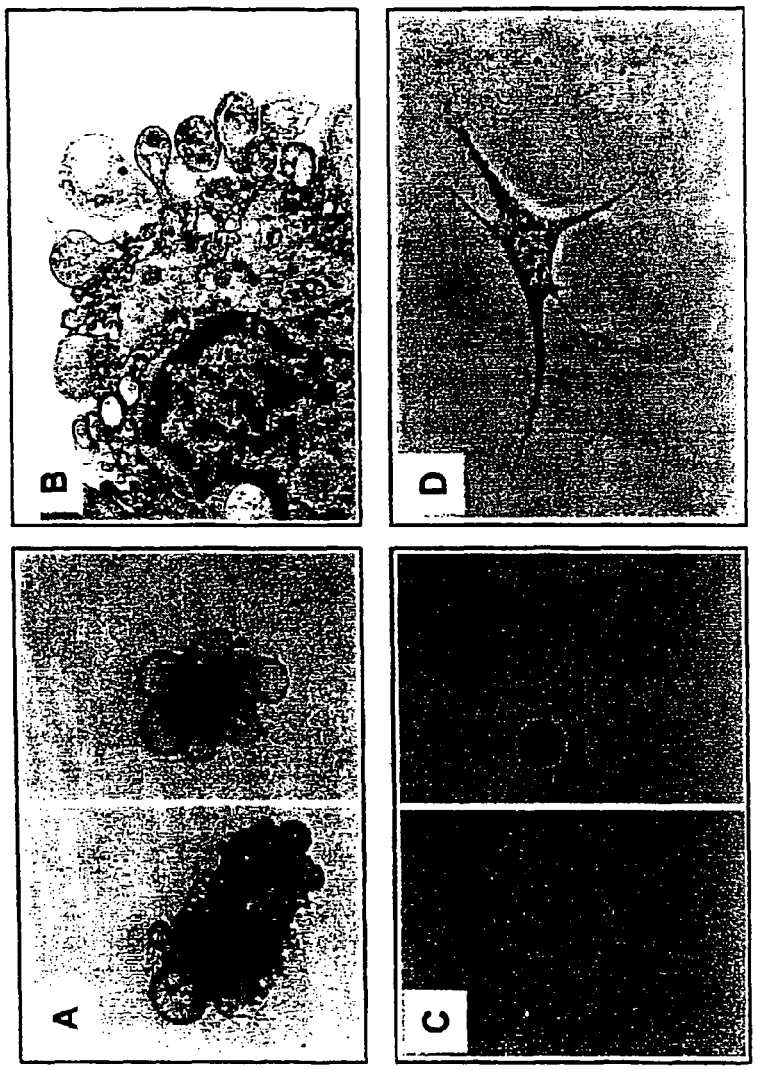

FIG. 3 Characterization of BM MPC. (A) Light microscopic examination of the freshly sorted cells revealed a homogenous population of large cells with heterochromatic nuclei and prominent mucleoli, a granular cytoplasm and numerous blel-like projetions of the cell membrane (magnified 40×). (B) Transmission electron micrograph of STRO-$1^{bright}$/VCAM-$1^+$ sorted cells isolated directly from BM (magnified 1000×). (C) Immunohistological staining of cytospin preparations of the sorted STRO-$1^{bright}$/VCAM-$1^+$ BMMNC showing intense staining of most cells with anti-collagen type I antibody, (magnified 40×). (D) Light microscopic view of a purified STRO-$1^{bright}$/VCAM-$1^+$, allowed to adhere to fibronectin-coated culture adopts a stellate, fibroblastoid morphology.

Figure 4:
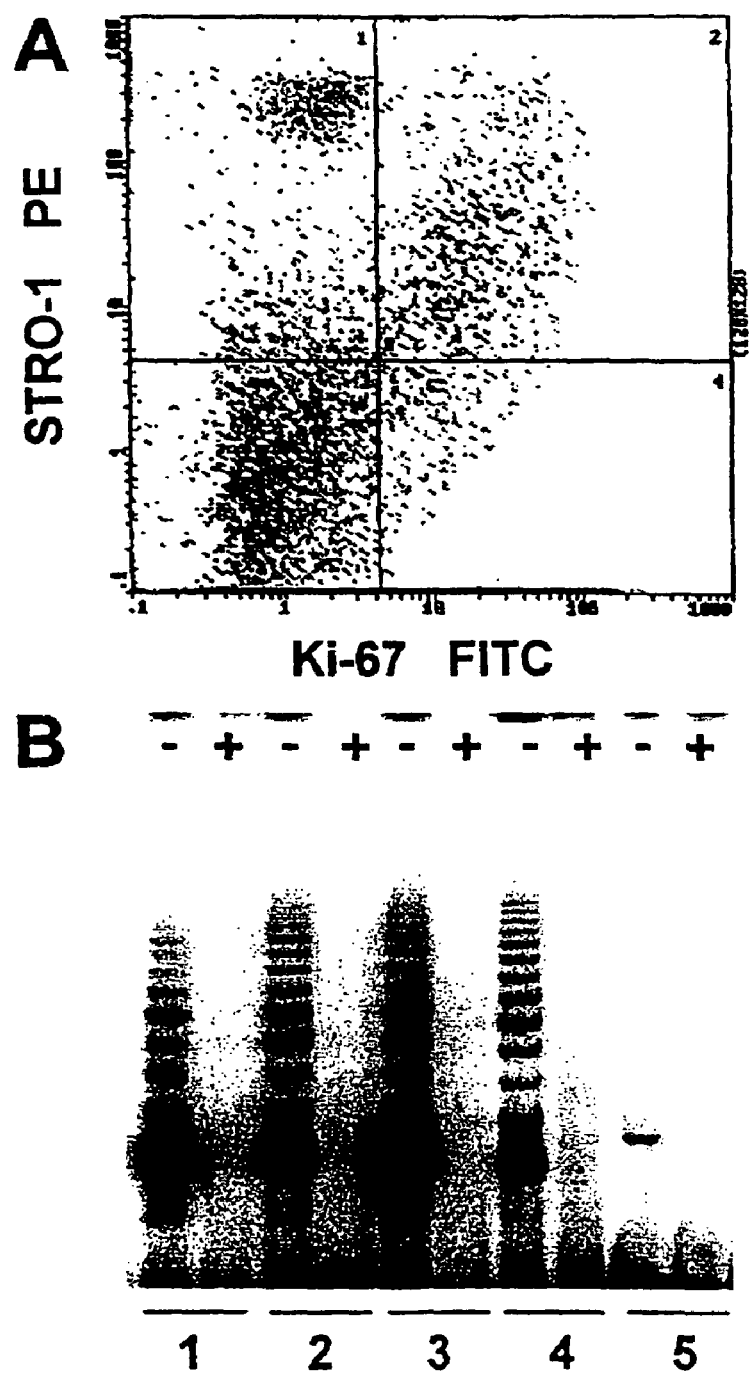

FIG. 4 Characterization of BM MPC. Dual-colour flow cytometric analysis of Ki67 (FITC) expression by STRO-$1^+$ (PE) BMMNC isolated by MACS. The dot plot histogram represents $5 \times 10^4$ events collected as listmode data (B). Telomerase activity in sorted cells populations was examined using a modified TRAP assay (C). TRAP products derived from CHAPS extracts of non-denatured (−) and denatured (+) total bone marrow (lanes 1 and 2), Total STRO-1 [MACS-selected] (lanes 2 and 3). STRO-$1^{bright}$/VCAM-$1^+$ cells sorted fraction (lanes 4 and 5), cultured. STRO-$1^{bright}$/VCAM-$1^+$ cells (lanes 6 and 7) and CD34$^+$-sorted cells TRAP products were resolved on a 12% polyacrylamide gel, stained with SYBR green fluorescent dye, and visualised using a fluorescence scanning system.

Figure 5:
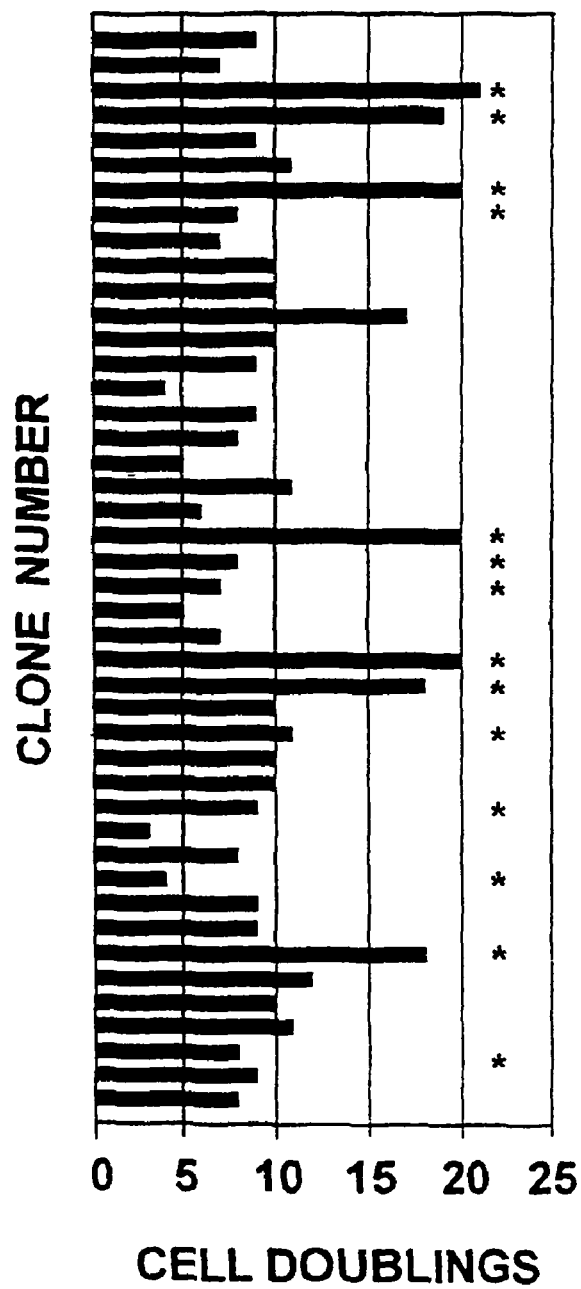

FIG. 5 A total of 44 CFU-F colonies derived from two BM samples were analysed for their cumulative production of cells. A marked variation in proliferative capacity between individual MPC is evident. The majority of clones (36/44; 82%) exhibited only moderate growth potential which did not persist beyond 12 population doublings. 8/44 clones (18%) demonstrated continued growth extending beyond 17 doublings. All clones were switched to adipogenic growth conditions, and under these conditions, 14/44 clones (32%) exhibited adipogenesis.

Figure 6:
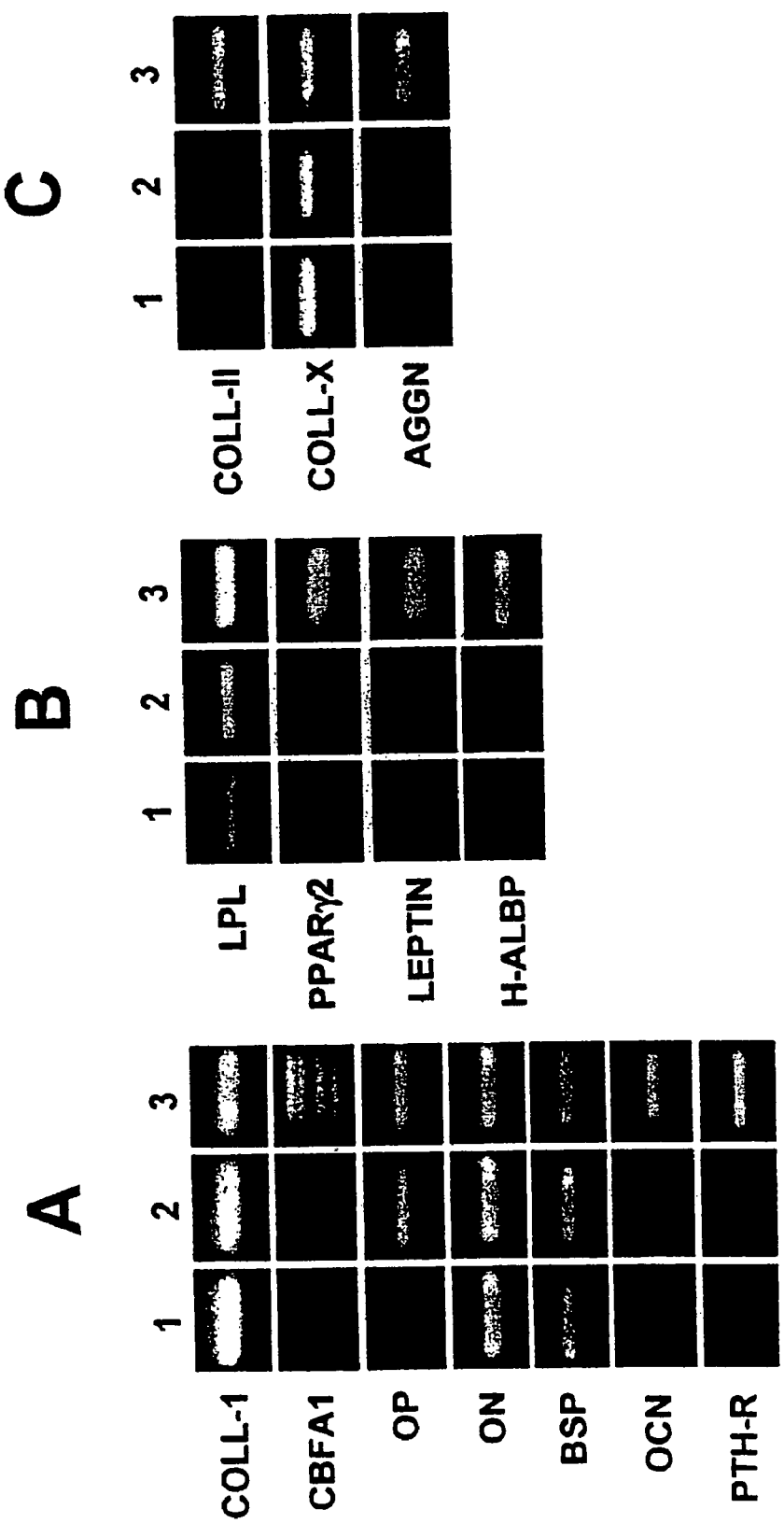

FIG. 6 RT-PCR analysis of gene expression in STRO-$1^{bright}$/VCAM-$1^+$ purified stromal precursor cells (MPC) isolated directly from marrow aspirates, non-induced primary stromal cultures derived from MPC (CFU-F), and CFU-F cultured under osteogenic-(BONE), chondrogenic-(CART) and adipogenic-(FAT) inductive growth conditions. Various markers of: BONE [transcription factor CBFA1; collagen type I (COLL-I); bonesialoprotein (BSP); osteopontin (OP); osteonectin (ON); osteocalcin (OCN), parathyroid hormone receptor (PTHR)]; FAT [lipoprotein lipase (LPL), transcription factor PPARγ2, leptin, human adipocyte lipid binding protein (H-ALBP)]; CARTILAGE [collagen type II (COIL-II), collagen type X (COLL-X), Aggrecam (AGGN)]. Reaction mixes were subjected to electrophoresis on a 1.5% agarose gel and visualised by ethidium bromide staining.

Figure 7:
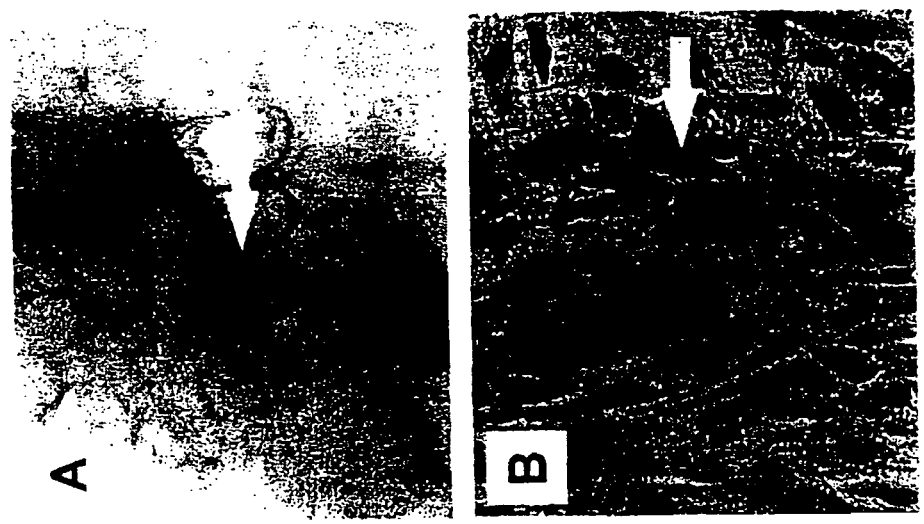

FIG. 7 In vitro developmental potential of MPC. Primary cultures of derived from STRO-$1^{bright}$/VCAM-1+ BMMNC were cultured for 2 weeks then induced under either osteogenic, adipocytic or chondrocytic conditions for 3-5 weeks. A von Kossa positive mineralised matrix formed throughout the cultures within 4 weeks of bone induction (200×) (A). The presence of clusters of lipid containing adipocytes were also detected by oil red-O staining (200×) (B). Cultures were counter stained with haematoxylin.

Figure 8:
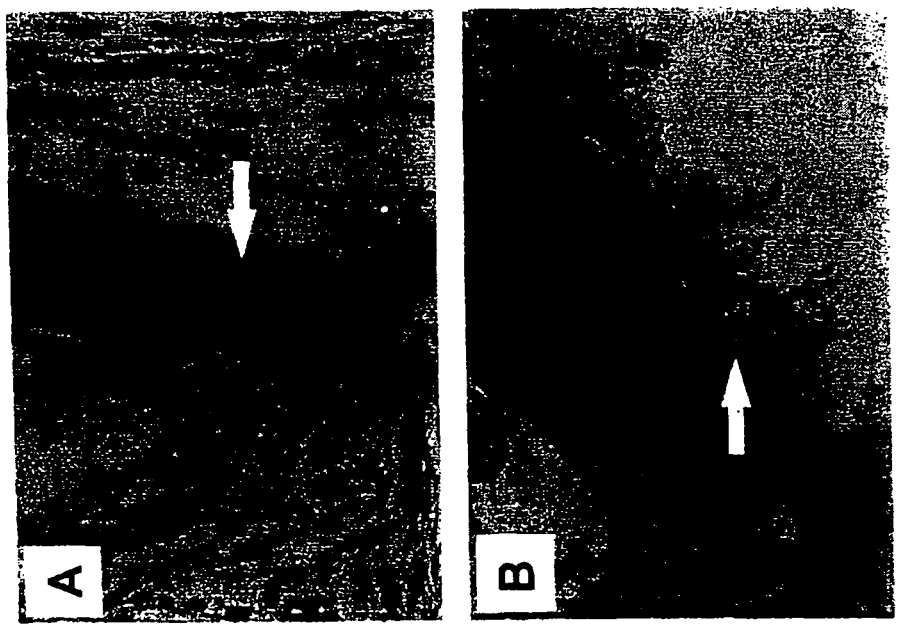

FIG. 8 New bone formation in vivo. Immunoselected STRO-$1^{bright}$/VCAM-$1^+$ BMMNC clones, expanded in vitro, were implanted subcutaneously into SCID mice using porous ceramic cubes. Implants were harvested 8 weeks post transplant. New bone formation (solid arrow) was observed for a proportion of clones within the cavities of the ceramic cubes (open arrow) together with surrounding fibrous and hematopoietic tissue (40×) (A). The sections were counter stained with haematoxylin and eosin. A magnified view of new bone formation is shown depicting an osteocyte (arrow) (200×) (B).

Figure 9:
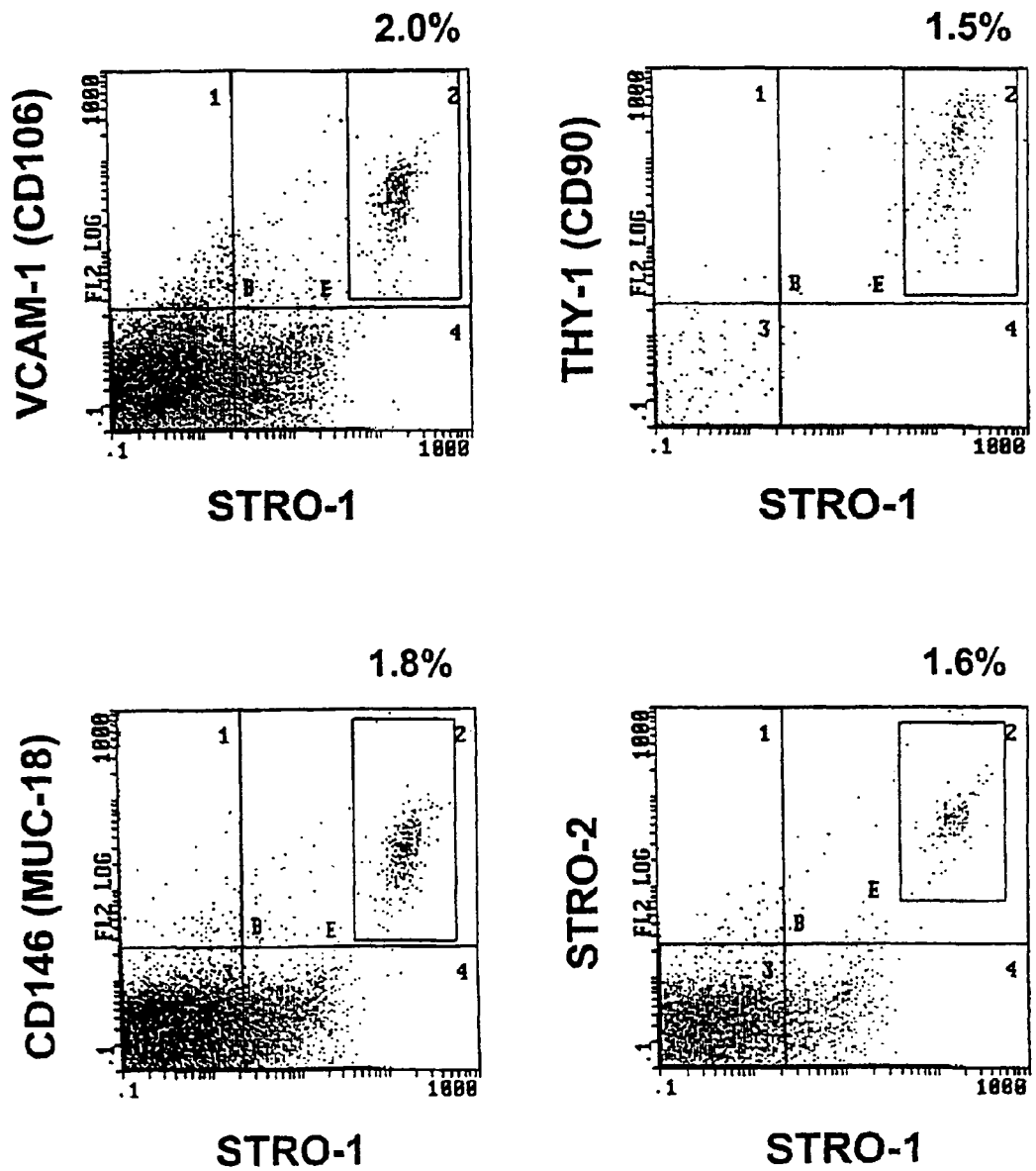

FIG. 9 Dual parameter flow cytometric analysis of STRO-$1^+$ human bone marrow mononuclear cells isolated by MACS. A distinct subpopulation of STRO-$1^{bri}$ cells are identified by VCAM-1, THY-1 (CD90), MUC-18 (CD-146) and STRO-2.

To properly investigate the biology of BM MPC, studies were designed to isolate MPC from a heterogeneous population of unfractionated BM cells. This was achieved by using a combination of positive immunoselection procedures based on the unique specificity of the STRO-1 mab, in order to maximise the recovery and purity of the MPC population. Following the isolation of homogeneous populations of MPC we then explored their pattern of gene expression for various bone-, fat- and cartilage-related markers to determine the degree of commitment towards different stromal cell lineages in vivo. Finally we have investigated the developmental potential of purified populations of BM MPC in vitro under defined conditions [Gronthos et al, 1994] and in vivo by ectopic implantation into immunodeficient mice [Haynesworth et al, 1992].

We and others have had success in isolating MPC based on their expression of the STRO-1 antigen either by FACS or by using immunomagnetic particles, such as Dynabeads [Tamayo et al, 1994] or by magnetic-activated cell sorting (MACS) [Gronthos et al, 1995 and 1998]. The latter was used initially to provide a reproducible technique for isolating BM derived MPC with the capacity to process high cell numbers. The mab STRO-1 proved to be an ideal reagent for isolating MPC from adult BM because of its lack of reactivity to haemopoietic progenitors [Simmons and Torok-Storb, 1991a] yielding a clean separation between MPC and haemopoietic progenitors in adult BM. Moreover, the antigen identified by STRO-1 was found in the present study to be expressed at particularly high copy number by MPC, which may in part account for the high efficiency and recovery of BM CFU-F observed. These studies identified the minor STRO-1$^{bright}$ subset of the total STRO-1$^+$ BMMNC fraction to contain the CFU-F population. However the resulting post MACS STRO-1$^{bright}$ cell population was only partially enriched for MPC.

We have previously demonstrated that the cell surface antigen, VCAM-1 is universally expressed on BM MPC and their progeny [Simmons et al, 1992, 1994]. This is in contrast to other markers expressed by BM MPC such as THY-1, CD10, CD13, and thrombomodulin, [Simmons et al, 1994] which are also known to react with either haemopoietic cells and or platelets [Baum et al, 1992; Conway and Nowakowski, 1993; Ship and Look, 1993]. The VCAM-1 molecule is a transmembrane glycoprotein with a molecular weight of between 95 and 110 kDa present on the membranes of stromal cells and endothelial cells [Osbom et al, 1989; Simmons et al, 1992]. The immunoglobulin super family member is one ligand for the integrin receptor α4β1 (VLA-4) present on haemopoietic stem cells, and is involved in the recruitment of lymphocytes and monocytes expressing α4β1 to sites of infection and inflammation [Elices et al, 1990; Simmons et al, 1992]. Significantly, VCAM-1 only reacted with a minor proportion of BMMNC effectively subletting the total STRO-1$^+$ population, reacting preferentially with the STRO-1$^{bright}$ cell fraction. The BM MPC population was subsequently shown to reside exclusively in the STRO-1$^{bright}$/VCAM-1$^+$ fraction of human adult BM.

The absolute frequency of MPC in bone marrow was determined by limiting dilution experiments using Poisson distribution statistics. Other studies using this statistical analysis have shown that murine BM osteoprogenitor cells with the potential to form mineralized bone nodules in vitro, occurred at a frequency of 1 per 1000 BM cells plated, based on the phenotype 5-fluoracil resistant, haemopoietic lineage marker negative [Van Viasselaer, 1994]. These osteoprogenitors represented approximately 20% of the total MPC population in normal murine BM [Falla et al, 1993; Van Vlasselaer, 1994]. Similar analyses of human BMMNC demonstrated the frequency of MPC at 1 per 1,000 to 1 per 100,000 cells plated, at 14 weeks and 24 weeks gestation, respectively, based on the inmmunophenotype CD34$^+$/CD38$^-$/HLA-DR$^-$ [Waller et al, 1995a]. Furthermore, additional subletting of fetal BM using the haemopoietic marker CD50, distinguished HSC from the MPC population, but found no significant difference in the incidence of clonogenic stromal cells sorted on the basis of the phenotype CD34$^+$/CD38$^-$/HLA-DR$^-$/CD50$^-$ [Waller et al, 1995b]. However, no stromal progenitors were observed when single cells of human adult BM samples were sorted based on the CD34$^+$/CD38$^-$/HLA-DR$^-$ phenotype [Waller et al, 1995a]. This may be due to the inefficiency of a predominantly negative selection criteria used to isolate fetal BM MPC and may also reflect the use of the CD34 antigen which demonstrates low level expression on adult BM MPC [Simmons and Torok-Storb, 1991b].

In the illustrated embodiment, the incidence of clonogenic cells (clusters 10<50 cells+colonies 50) from adult human BM was determined to be 1 per 2 STRO-1$^{bright}$/VCAM-1$^+$ cells plated in SDM containing PDGF and EGF. Using serum-deprived medium significantly enhances the incidence of clonogenic growth over that of serum replete cultures, particularly at low plating densities [Gronthos and Simmons, 1995]. It must also be stated that a proportion of the wells which were scored as 'negative' contained cell clusters of less than 10 cells. Therefore, by further refining the CFU-F culture assay, it may be possible to stimulate the growth of MPC in order to increase the overall purity of the MPC population based on the composite STRO-1$^{bright}$/VCAM-1$^+$ phenotype. Nevertheless, the combined purification technique of the illustrated embodiment effectively achieved a several thousand fold increase in the incidence of BM MPC when compared to unfractionated BMMNC.

The cells contained within the STRO-1$^{bright}$/VCAM-1$^+$ BM fraction were found to be a homogeneous population of large cells with extensive cytoplasmic processes existing in vivo in a non-cycling state. Other studies have found that MPC residing in the BM are almost entirely non-cycling as shown by $^3$H thymidine labelling in rodents and by means of the in vitro thymidine suicide technique in humans [Castro-Malaspina et al, 1980; Castro-Malaspina et al, 1981]. This data coincides with the observations that primitive multi-potential stem cells, identified in the other cell systems such as HSC are by definition quiescent cells [Andrews et al, 1986; Szilvassy et al, 1989; Li and Johnson, 1992]. Given the reported developmental potential of cultured BM MPC in vitro and in vivo the question arises as to whether these cells are truly representative of an early uncommitted phenotype with multi-potential or whether all or a proportion of the CFU-F are already committed towards a particular stromal cell lineage.

Analysis of the gene expression pattern of purified adult BM MPC in the illustrated embodiment has revealed that many of the genes expressed by CFU-F in vivo demonstrate a broad stromal tissue distribution related to osteoblasts, adipocytes and chondrocytes. It is very common to find in the literature that many markers for example osteonectin, osteopontin, and alkaline phosphatase in the bone cell lineage are described as being specific to bone cells, when in fact these markers have a wider tissue distribution. Therefore, it is not surprising to find that MPC identified by STRO-1 share common markers with differentiated stromal cell types. Importantly, specific markers of commitment such as CBFA-1, collagen type II, PPARγ2, [reviewed in Rodan and Harada, 1997] to bone, cartilage and fat respectively were not expressed by the STRO-1$^{bright}$/VCAM-1$^+$ population in fresh BM aspirates. In addition, immunohistochemical examination of STRO-1$^{bright}$/VCAM-1$^+$ sorted BMMNC failed to show any reactivity to the smooth muscle marker α-smooth muscle actin or with the endothelial marker, FVIII. Therefore the MPC residing in the BM seem to exist in an uncommitted state, and may have the potential under different conditions to develop into a few or all of the stromal elements recognised in the bone marrow microenvironment.

In the present study, cultures of purified STRO-1$^{bright}$/VCAM-1$^+$ human BM CFU-F typically developed a von Kossa positive mineral by twenty one days under osteogenic conditions (ASC-2P, PO$_{4i}$, DEX). The presence of mineral deposits was demonstrated in all CFU-F clones examined, where 40% of the clones also displayed the capacity to differentiate into adipocytic cell clusters. Moreover, individual CFU-F clones were also found to contain a small proportion of fibroblastic-like cells not associated with either mineralization or lipid accumulation. These fibroblast-like cells may represent as yet undefined stromal populations such as reticular cells, smooth muscle cells, bone lining cells, osteocytes and committed stromal progenitors.

The developmental potential of selected CFU-F clones was further examined in vivo. The porous hydroxyapatite coated ceramic cubes reproducibly supported the development of human osteogenic tissue in SCID mouse. This is in agreement with the findings in previous in vivo studies using unfractionated rodent and human BM mesenchymal cell cultures [Haynesworth et al, 1992a; Krebsbach et al, 1997; Kusnetsov et al, 1997]. In the present study, pretreating the HA ceramic cubes with purified fibronectin was critical to maximise the number of cells retained in the cubes after loading prior to transplantation (data not shown). Pre-treatment of HA cubes with fibronectin and lamninin has been reported to increase cell retention and spreading on the ceramic surface of the cubes [Dennis et al, 1992; Dennis and Caplan; 1993]. Fibronectin and laminin coated cubes were found to augment bone formation from cultured rat BM mesenchymal cells at earlier time points in comparison to untreated cubes [Dennis et al, 1992; Dennis and Caplan, 1993].

The present study failed to detect cartilage formation in any of the transplantation models used, in contrast to other studies which demonstrated cartilage formation in diffusion chambers transplanted with rodent bone marrow or mesenchymal cells derived from the marrow of young children. To date, there have been no reports describing the reproducible induction of cartilage formation using adult human bone marrow stromal cells in vivo or in vitro. In the present study, the expression of the hypertrophic chondrocyte marker collagen type X, by purified adult human BM MPC, is somewhat puzzling, given the presumed specificity of this molecule. Since the physiological role of collagen type X is unknown, its significance in bone marrow remains to be determined.

The present work is in accord with previous studies showing that the formation of new bone in implants of HA cubes is attributed to differentiation of human mesenchymal cells into functional osteoblasts [Kusnetsov et al, 1997] and did not result from the recruitment of osteoprogenitors from the surrounding host (mouse) tissue. Furthermore, other cell types present such as muscle, adipocytes and vascular endothelial cells showed no hybridization with the alu probe and are therefore presumed to be host in origin. These findings demonstrate that a proportion of BM MPC within the STRO-$1^{bright}$/VCAM-$1^+$ BM subfraction, demonstrate the capacity to develop into multiple stromal cell types including osteoblasts, adipocytes and fibroblast-like cells.

Further subletting of the STRO-$1^{bright}$/VCAM-$1^+$ BM fraction using three- and four-colour FACS analysis may eventually provide a means to discriminate between subpopulations contained within the MPC pool which exhibit different developmental potentials. The purification of MPC clones with different potential may then be used to generate multipotent, bi-potent and uni-potent cell lines which could greatly facilitate the design of experimental approaches to study the molecular mechanisms regulating the commitment of early precursors into different stromal cell lineages.

One area of potential benefit that will occur from a greater understanding of the proliferation and differentiation of MPC, is the ability to manipulate and expand mesenchymal cell populations in vitro for subsequent reimplantation in vivo. The use of animal models has demonstrated the efficacy of utilising ex vivo expanded BM mesenchymal cells to facilitate bone regeneration and tendon repair in vivo [Bruder et al, 1998b; 1998c; Young et al, 1998]. Several studies have also described how cultured marrow stromal cells from a variety of species are readily infected using either amphotropic retroviruses or adenoviruses [Harigaya and Handa, 1985; Rothstein et al, 1985; Singer et al. 1987; Cicutinni et al, 1992; Roecklein and Torok-Storb, 1995]. In addition, some studies have demonstrated the persistence of transplanted transduced cells over several months in animal models [Li et al, 1995; Anklesaria et al, 1996; Onyia et al, 1998 Reiw et al, 1998].

Therefore the ability to harvest purified human MPC from aspirates of BM and to expand these cells ex vivo makes them ideal candidates as possible vehicles for gene transfer, in order to treat a variety of diseases and genetic disorders.

Materials and Methods

Subjects

Aspirates of human BM samples were obtained from the iliac crest and the sternum of normal adult volunteers with their informed consent, according to procedures approved by the ethics committee at the Royal Adelaide Hospital, South Australia. Bone marrow mononuclear cells (BMMNC) were obtained by centrifugation over Ficoll 1.077 g/ml (Lymphoprep, Nycomed, Oslo, Norway) at 400 g for 30 minutes (min) and then washed and resuspended with Hank's buffered saline solution containing 1% bovine serum albumin and 10 mM HEPES, pH 7.35 (HBSS).

Isolation of STRO-1+ Cells by Magnetic-Activated Cell Sorting (MACS)

This procedure is a modification of that described elsewhere [Gronthos et al, 1998]. Approximately $1\times10^8$ BMMNC were incubated with STRO-1 supernatant for 60 min on ice. The cells were then washed in HBSS and resuspended in 1 ml of HBSS containing a 1/50 dilution of biotinylated goat anti-mouse IgM (µ-chain specific; Southern Biotechnology Associates, Birmingham, Ala.) for 45 min on ice. Following this, the cells were washed twice in MACS buffer (single strength $Ca^{2+}$ and $Mn^{2+}$ free PBS supplemented with 1% BSA, 5 mM EDTA and 0.01% sodium azide) and resuspended in 900 µl of MACS buffer to which 100 µl of streptavidin microbeads (Miltenyi Biotec, Bergisch Gladbach, F.R.G.) was added. The cells were further incubated for 15 min on ice after which streptavidin-fluorescein isothiosyanate (FITC) conjugate (1/50; Caltag Laboratories, San Francisco, Calif.) was added directly to the suspension for an additional 5 min. The cells were separated on a Mini MACS magnetic column (column capacity $10^7$ cells, Miltenyi Biotec) according to the manufacturers specifications.

Purification of the CFU-F Population by Fluorescence Activated Cell Sorting (FACS)

Dual colour-FACS analysis of the STRO-$1^{bright}$ population was achieved by incubating the MACS isolated STRO-1 population with saturating levels of the Mab 6G10 (mouse IgG1 anti-human CD 106: vascular endothelial adhesion molecule-1, VCAM-1; kindly donated by Dr. B. Masinovski FCOS Corp., Seattle Wash.) for 30 min on ice. After washing with HBSS the cells were incubated with a second label goat anti-mouse IgG (γ-chain specific) phycoerythrin (PE) conjugate antibody (1/50; Southern Biotechnology Associates, Birmingham, Ala.) and a streptavidin-FITC conjugate (1/50; CALTAG Laboratories, San Francisco, Calif.) for 20 min on ice. The cells were then washed in HBSS prior to being sorted using the automated cell deposition unit (ACDU) of a FACStar$^{PLUS}$ (Becton Dickinson, Sunnyvale, Calif.) flow cytometer. STRO-$1^{bright}$/VCAM-1+ cells were seeded at plating densities of 1, 2, 3, 4, 5, and 10 cells per well (96-well plates) in replicates of 24 wells per plating density (FIG. 2). The cells were cultured in serum deprived medium on fibronectin coated wells as previously described [Gronthos and Simmons 1995; Gronthos et al, 1998]. On day 10 of culture the cells were then fixed and stained for 60 min with 0.1% toluidine blue in 1% paraformaldehyde. Aggregates of 50 cells were scored as CFU-F colonies and aggregates of 10<50 cells were scored as clusters using an Olympus SZ-PT dissecting light microscope (Olympus Optical Co. Ltd, Tokyo, Japan).

Analysis of Cell Cycling Status of STRO-1+ BMMNC

The STRO-$1^+$ BMMNC were isolated by MACS as described above and then incubated with streptavidin PE for 15 min on ice. After washing twice with PBS the cells were fixed for 10 min with cold methanol (70%) on ice. Following this, the cells were washed three times with PBS and then incubated in blocking buffer for 15 minutes. The monoclonal antibody Ki-67 conjugated to FITC (DAKOPATTS A/S, Glostrup, Denmark) was added directly to the cells (1/10 dilution) in blocking buffer for 45 min on ice served as the negative control.

RNA Isolation and First-Strand cDNA Synthesis

Total cellular RNA was routinely prepared from $2 \times 10^4$ STRO-$1^{bright}$/VCAM-$1^+$ cells collected as a bulk population and lysed using RNAzolB extraction method (Biotecx Lab. Inc., Houston, Tex.), as per manufacturers recommendations. RNA isolated from each subpopulation was then used as a template for cDNA synthesis. cDNA was prepared using a First-strand cDNA synthesis kit from Pharmacia Biotech (Uppsala, Sweden) according to manufacturers instructions. Briefly, total RNA was resuspended in 8 µl of DEPC-treated water and subsequently heated to 65° C. for 10 min. Following snap cooling on ice, the RNA was added to 7 µl of premix containing reaction buffer, oligo-dT as primer and Superscript MMLV Reverse transcriptase. Following incubation at 42° C. for 60 min, the volume of the reaction was adjusted to 50 µl with the addition of 35 µl of sterile water. The samples were stored at −20° C.

Polymerase Chain Reaction (PCR)

Due to limiting cell numbers, the expression of various bone-related transcripts (Table I) was assessed by polymerase chain reaction (PCR) amplification, using a standard protocol [Sambrook et al, 1989]. Two microliters of first strand cDNA mixture from each subpopulation was diluted in a 50 µl PCR reaction (67 mM Tris HCl pH 8.8, 16.6 mM $(NH_4)_2SO_4$, 0.45% Triton X100, 200 µg/ml gelatin, 2 mM $MgCl_2$, 200 µM each dNTP) containing 100 ng of each primer (Table 1), to which 2.5 units of Amplitaq Polymerase (Perkin-Elmer, Norwalk, Conn., USA) was added. Reaction mixes were overlayed with mineral oil and amplification achieved by incubation in a Perkin-Elmer/Cetus thermal cycler. Primer design enabled typical cycling conditions of 94° C./(2 min), 60° C./(30 sec), 72° C./(1 min) for 40 cycles, with a final 10 min incubation at 72° C. To control for the integrity of the various RNA preparations, the expression of GAPDH and/or beta-2-microglobulin was also assessed. Following amplification, 10 µl of each reaction mixture was analysed by 1.5% agarose gel electrophoresis, and visualised by ethidium bromide staining.

The Developmental Potential of BM CFU-F In Vitro

We have previously reported the conditions for the induction of human bone marrow stromal cells to develop a mineralised bone matrix in vitro [Gronthos et al, 1994]. Briefly, the osteogenic and adipocytic potential of thirty day 4 CFU-F clones derived from single STRO-$1^{bright}$/VCAM-$1^+$ sorted cells was assessed by culturing in alpha modification of Eagle's medium (α-MEM: Flow Laboratories) supplemented with 20% FCS, L-glutamine (2 mM), β-mercaptoethanol ($5 \times 1^{-5}$ M), L-ascorbic acid 2-phosphate (100 pM) (ASC-2P: Novachem, Melbourne, Australia), dexamethasone sodium phosphate ($10^{-8}$M) (DEX: David Bull Laboratories, Sydney, Australia), $KH_2PO_4$ (1.8 mM) (BDH Chemicals) and Hepes (10 mM), at 37° C., 5% $CO_2$. The media was changed twice a week for a period of six weeks. Cultures were rinsed twice with PBS then fixed in situ with 10% neutral formalin for 30 mon. Staining for vonKossa was performed according to the method of Pearse and Gardner (1972). Sections or culture wells were washed twice in distilled water and then stained in 5% aqueous $AgNO_3$ for 60 min under ultraviolet light. After staining with $AgNO_3$, the sections were washed twice with distilled water and then placed in 5% sodium thiosulphate for 1 min. Cultures were washed in distilled water, counter stained with Mayer's haematoxylin and mounted. Oil Red O (ORO) staining was performed as described by Grimble (1998). Briefly, cultures were fixed as described above, washed twice with PBS and air dried. Cultures were immersed in a solution 0.5% (w/w) ORO in isopropanol for 15 min at room temp., washed three times with distilled water and subsequently counterstained with haematoxylin.

Similarly, the chondrogenic potential of the same clones was assessed by culturing $2 \times 10^5$ cells per clone in 0.5 mls SDM supplemented with TGFβ1 and gently centrifuged at 200 g for 2 min in a 10 ml polypropolene tube then incubated at 37° C., 5% $CO_2$. The media was changed twice a week for a period of three weeks The Developmental Potential of BM CFU-F In Vivo Bulk cultures of CFU-F derived from STRO-$1^{bright}$/VCAM-$1^+$ sorted BMMNC were cultured for 5 weeks in the presence of ASC-2P and DEX and 10% FCS. The adherent cell layers were trypsinised and seeded onto 27 mm$^3$ porous hydroxyapatite ceramic cubes (Zimmer Corporation, Warsaw, Ind., USA) pre-coated with fibronectin (5 µg/ml) (Boehringer Mannheim, Germany). The ceramic cubes were then implanted into subcutaneous pockets into the backs of SCID mice for a period of up to 8 weeks as described previously [Haynesworth et al, 1994; Kuznetsov et al, 1997]. Recovered implants were fixed in 10% buffered formalin for 2 days then decalcified for a further seven days in 0.5M EDTA before being embedded in paraffin wax. Cross-sections of the cubes were prepared as 5 µm sections onto glass slides pre-coated with Cell-Tak and counter stained with haematoxylin and eosin.

In Situ Hybridization for the Human Specific alu Sequence

The HA ceramic implants were recovered 8 weeks post transplant and prepared for paraffin embedding on Cell-Tak coated slides as described above. To determine the origin of the cells within the implants in situ hybridization analysis was performed using a probe specific to the unique human repetitive alu sequence [Kuznetsov et al, 1997]. The human specific alu sequence (pBLUR8; ATCC) was subcloned into the BamH1 restriction site of a pGEM-4Z plasmid (Promega). The digoxigennin-labeled alu specific probe was prepared by PCR containing 1×PCR buffer (67 mM Tris HCl pH 8.8, 16.6 mM $(NH_4)_2SO_4$, 0.5% Triton-X100, 0.2 µg/ml gelatin, 2.5 mM $MgCl_2$, 0.2 mM dATP, 0.2 mM dCTP, 0.2 mM dGTP, 1.9 mM dTTP, 0.1 mM digoxygenin-11-dUTP (Boehringer Mannheim), and 0.25 units of Amplitaq Polymerase) and 100 ng of SP6 and T7 primers (Table 1) and 1 ng of plasmid (pGEM-4Z; Promega Corp., Madison, Wis.) containing the alu sequence subcloned into the BamHI restriction site from (pBLUR8; ATCC, Rockville, Md.). Sections were deparaffinized with xylene and ethanol then rehydrated through graded (100%, 90%, 70%, 50%) ethanol solutions. The sections were then treated with 0.2N for 7 min at room temperature and then incubated in 1 mg/ml pepsin (Sigma, St. Louis, Mo.) in 0.1N HCl for 10 minutes at 37° C. After washing in PBS, the sections were treated with 0.25% acetic acid containing 0.1M triethanolamine (pH 8.0) for 10 min and prehybridized with 50% deionized formamide containing 4×SSC for 15 min at 37° C. The hybridization solution (1 ng/µl digoxigenin-labeled probe in 1×Denhardt's solution, 5% dextrane sulfate, 0.2 mg/ml, salmon sperm DNA, 4×SSC, 50-% deionized formamide) was then added to the sections for denaturation at 95° C. for 3 minutes followed by hybridization at 45° C. for 3 hr. After washing with 2×SSC and 0.1×SSC, digoxigenin-labeled DNA was detected by immunohistochemistry using antidigoxigenin alkaline phosphatase-conjugated Fab fragments (1/5000; Boehringer Mannheim Corp., GMBH, Germany) followed by incubation with the corresponding alkaline phosphatase nitroblue tetrazolium/5-bromo-4-chloro-3-indolyl-phosphate substrate solution as recommended by Boehringer Mannheim. Micrographs were taken with Ektachrome 64 T colour film using an Olympus IMT-2 inverted light microscope.

Telomerase Repeat Amplification Protocol (TRAP) Assay

Telomerase activity was measured by a modified non-radioactive TRAP protocol essentially as described by Fong et al (1997). Telomerase cell extracts were prepared by the method of Kim et al, (1994), with minor modifications. Populations of sorted or cultured cells were lysed in ice-cold CHAPS extraction buffer (0.5% 3[(3-cholamidopropyl)-dimethyl-ammonio]-1-propanesulfonate], 50 mM Tris-HCI, pH 7.4, 5 mM $MgCl_2$, 5 mM EGTA, 25 mM 2-mercaptoethanol, 1 ng/ml leupeptin, and 50% glycerol in DEPC-treated water), at a concentration of 1000 cells/µl, incubated on ice for 30 minutes and centrifuged at 16000×g for 20 minutes at 4° C., the supernatant recovered and stored at −80° C. until required. Detection of telomerase activity was performed in a two-step process as previously described (Fong et al, 1997). Briefly, to 2 µl of cell extract, 16.5 µl of TRAP reaction buffer (20 mM Tris-HCI, pH8.2, 1.5 mM $MgCl_2$, 63 mM KCl, 0.05% Tween-20, 1 mM EGTA), 100 ng of each of TS primer (5'-AATC-CGTCGAGCAGAGTT-3') (SEQ ID NO. 1), and CX-ext primer (5'-GTGCCCTTCCCTTACCCTTACCC TAA-3') (SEQ ID NO. 2), 0.5 µL dNTPs (10 mM stock) were added, and the reaction mix incubated at 25° C. for 30 minutes. Telomerase was subsequently inactivated by heating the reaction to 90° C. for 2 minutes, prior to the addition of 5 µl of PCR mixture, containing 3.5 µl of TRAP reaction buffer, 1 µl of CX-ext primer and 2.5 U Taq polymerase. Reaction mixes were covered with mineral oil and placed in a Hybaid thermocycler, and subjected for 34 cycles of 94° C. for 30 seconds, 50° C. for 30 seconds and 72° C. for 45 seconds, with a final extension at 72° C. for 2 minutes. To confirm the specificity of the telomerase products, in all cases, a 2 µl aliquot of each CHAPS lysate was subjected to denaturation by heating samples at 100° C. for 10 minutes 25 µl of each reaction was resolved on a non-denaturing 12% polyacrylamide gel, and visualized by staining width SYBR Green fluorescent dye (FMC Bioproducts, OR, USA) as recommended by the manufacturer. The TRAP products were analysed using a fluorescence scanning system (Molecular Dynamics, Sunnyvale, Calif., USA).

Transmission Electron Microscopy (TEM)

STRO-1$^{bright}$/VCAM-1$^+$ cells (approximately 2×10$^4$ cells) were collected as a bulk population into eppendorf microtubes, washed once in 0.05M sodium cacodylate buffer and then fixed in 2.5% glutaraldehyde (EM Grade) in cacodylate buffer for 2 hr. The cultures were postfixed with 2% osmium tetroxide (VIII) (BDH Chemicals) in cacodylate buffer for 1 hr. After this, the cultures were dehydrated with graded ethanol solutions (70%, 90%, 100%). Epoxy resin (TAAB Laboratories; Berkshire, England) was then used to infiltrate the cultures overnight at 37° C. Polymerization of the resin was carried out at 60° C. for 24 hr under vacuum. Ultrathin sections were cut on a LKB 8800 Ultrotome II (Broma, UK) and mounted onto copper grids. Sections were then examined using a JEOL 1200 EX II (Tokyo, Japan) transmission electron microscope. Photographs were taken using ILFORD EM Technical film.

Results

Isolation and Purification of STRO-1$^+$ BM MPC

We have previously demonstrated the effectiveness of MACS to isolate and enrich for MPC from aspirates of human BM based on the cell surface expression of the STRO-1 antibody [Gronthos and Simmons, 1995; Gronthos et al, 1998]. In the present study, flow cytometric analysis of MACS isolated STRO-1$^+$ BMMNC cells demonstrated a heterogeneous pattern of expression spanning over four logs in fluorescence intensity (FIG. 1). Single-color FACS was subsequently employed to sort the STRO-1$^+$ BMMNC fraction into three subsets; STRO-1$^{dull}$ STRO-1$^{intermediate}$ and STRO-1$^{bright}$ Clonogenic assay for CFU-F in the different sorted STRO-1$^+$ subpopulations demonstrated that the majority of the MPC were contained within the STRO-1$^{bright}$ cell fraction. There was a 900 fold increase in the incidence of CFU-F in the STRO-1$^{bright}$ population when compared to unfractionated BMMNC (Table 1) demonstrating that BM MPC contained a high copy number of the STRO-1 antigen on their cell surface. The recovery of the MPC population in the STRO-1$^{bright}$ fraction was >75% in respect to the estimated total number of CFU-F in the BM sample pre-MACS.

We attempted to obtain a more accurate discrimination of the STRO-1$^{bright}$ subset by incubating the total STRO-1$^+$ MACS isolated cells with the stromal cell surface antigen VCAM-1 (FIG. 2A) previously found to react exclusively with BM MPC [Simmons et al, 1994]. Dual color-FACS was used to identify and isolate the STRO-1$^{bright}$/VCAM-1$^+$ BMMNC fraction. Limiting dilution analysis was subsequently performed, using the FACStar$^{PLUS}$ automated cell deposition unit, to seed STRO-1$^{bright}$/VCAM-1$^+$ cells at various plating densities as described in the methods. Cells were cultured under serum deprived conditions in the presence of PDGF and EGF (10 ng/ml) previously found to support the clonogenic growth of CFU-F above that of serum replete conditions particularly at low plating densities [Gronthos and Simmons, 1995]. The mean incidence (n=6 different BM donors) of day 10 CFU-F colonies (>50 cells) was determined to be 1 CFU-F per 3 STRO1$^{bright}$/VCAM-1$^+$ cells plated using Poisson distribution statistics (FIG. 2B). Furthermore, the incidence of clonogenic cells (clusters>10<50 cells+colonies) was found to be 1 per 2 STRO-1$^{bright}$/VCAM-1$^+$ cells plated (FIG. 2C). The MACS/FACS purification technique effectively achieved a 5×10$^3$ fold enrichment of the CFU-F population when compared to unfractionated BMMNC with an average incidence of 1 CFU-F colony per 10$^4$ BMMNC. It must also be stated that a proportion of the wells which were scored as 'negative' contained cell clusters of less than 10 cells.

Characterization of Purified BM MPC

Morphological examination of freshly sorted STRO-1$^{bright}$/VCAM-1$^+$ cells was carried out by transmission electron microscopy. Purified BM CFU-F appeared to be a homogeneous population of large cells containing many cytoplasmic processes and a large nucleus with an open chromatin structure (FIG. 3). To determine the cell cycling status of the CFU-F population in aspirates of BM the MACS isolated STRO-1$^+$ BMMNC fraction was further incubated with the cell cycling specific antigen Ki-67 [Gerdes et al, 1984; Wersto et al, 1988]. Two color flow cytometric analysis revealed that the STRO-1$^{bright}$ subset which contained the CFU-F population lacked co-expression of the Ki-67 antigen demonstrating that these cells are non-dividing in vivo (FIG. 4A). Telomerase activity was examined in cell extracts from sorted and cultured candidate stromal progenitor cell populations by a modified TRAP assay. Telomerase activity was present in all fractions including the candidate stromal stem cell compartment isolated from adult bone marrow, defined by their expression of both the STRO-1 and VCAM-1 (CD106) cell surface molecules (FIG. 4B).

To assess the proliferative capacity of BM MPC, individual CFU-F colonies (n=44) derived from two BM samples were expanded in the presence of serum under normal clonogenic growth conditions. A minor proportion of clones (8/44, 18%) demonstrated continued growth extending beyond 20 population doublings while the remainder showed little or no proliferation beyond 12 population doublings (FIG. 5). These cells also appeared to be capable of differentiating into adipose cells, whereas other isolated cells were less likely to do so.

A detailed phenotypic analysis of freshly isolated BM MPC pre-culture was compiled. Total RNA obtained from STRO-1$^{bright}$/VCAM-1$^+$ cells was used to generate full-length first-strand cDNA as described in the methods. RT-PCR analysis revealed the presence of various bone cell markers including bonesialoprotein, osteonectin, and collagen type I. However, there was an absence in the expression of osteopontin, the parathyroid hormone receptor, and the more specific bone cell markers osteocalcin and the transcription factor CBFAI (FIG. 6A). Similarly, the fat-related markers lipoprotein lipase and the adipocyte human lipid binding protein were found to be expressed by the STRO-1$^{bright}$/VCAM-1$^+$ population but there was no detectable expression of the adipocyte specific markers, the obese gene product (leptin) and the early transcription factor PPARγ2 in these cells (FIG. 6B). Furthermore the cartilage specific markers collagen type II and aggrecan were also not expressed by our purified MPC population. However the STRO-1$^{bright}$/VCAM-1$^+$ cell fraction was found to express collagen type X, a marker associated with hypertrophic chondrocytes (FIG. 6C). In addition, cytospin preparations of STRO-1$^{bright}$/VCAM-1$^+$ sorted BMMNC failed to show any reactivity to the smooth muscle marker α-smooth muscle actin or with the endothelial marker, FVIII (data not shown). Overall the MPC population appeared to represent an early precursor population not yet fully committed to anyone particular stromal cell lineage.

Culture expanded bulk CFU-F derived from STRO-1$^{bright}$/VCAM-1$^+$ sorted cells were assessed for their ability to develop into functional osteoblasts, chondrocytes and adipocytes in vitro as previously described [Gronthos et al, 1994]. A von Kossa positive mineralised matrix developed throughout the cultures by the end of the sixth week of induction (FIG. 7A). In addition, clusters of Oil Red O positive adipocytes were observed within the adherent layers in the same cultures (FIG. 7B). Following three weeks of chondrocytic induction in the presence of TGFβ1, the cells were also found to express the cartilage specific marker collagen type II by immunohistochemistry. Furthermore RT-PCR analysis of total RNA isolated from the different culture conditions demonstrated the expression of markers specific to bone (CBFA-1, OCN, PTH-R), fat (PPARγ2, leptin) and cartilage (collagen type II, aggrecan) (FIG. 6B).

The Developmental Potential of BM MPC Clones In Vitro and In Vivo

Bone marrow CFU-F clones were established from STRO-1$^{bright}$/VCAM-1$^+$ sorted cells from three individual BM donors. At day 4 of culture, single clonogenic clusters were identified and expanded by subculture. Half of the cells from the first passage were taken from each clone and cultured under osteogenic growth conditions as described above. The osteogenic potential of ninety CFU-F clones was assessed where a von Kossa positive mineralised matrix formed in all of the ninety clones. However, only a proportion (38%±15SEM, n=3) of the same clones gave rise to clusters of lipid containing oil red-O positive adipocytes demonstrating the bi-potential of the CFU-F population in vitro.

Half the cells from a representative 46 clones were subcultured and expanded for several weeks, then seeded into porous HA ceramic cubes and implanted subcutaneously into SCID mice for a period of 8 weeks as previously described [Haynesworth et al, 1992, Kusnetsov et al, 1997]. Cross-sections of the cubes prepared for histological examination showed that all of the implants contained an extensive network of blood vessels and fibrous tissue (FIG. 8A and FIG. 8B). Bone formation was found in 42% (n=26) and 55% (n=20) of the clones isolated from two different BM aspirates. The ability of individual MPC clones to form a von Kossa positive mineralised matrix in vitro did not always correlate to the development of new bone in vivo. Similarly, the capacity of MPC clones to form adipocytic clusters in vitro had no bearing on the development of new bone formation in vivo.

The origin of the cellular material within the recovered implants was assessed by in situ hybridization using a probe specific to the unique human repetitive alu sequence. The fibrous tissue, bone lining cells and osteocytes within the newly formed bone were all found to be positive for the alu sequence confirming their human origin and the bi-potential of a proportion of BM MPC (FIG. 9C and FIG. 9D). Conversely, the fat and smooth muscle surrounding the ceramic cubes did not express the alu sequence and was therefore presumed to have originated from the host. Similarly, the endothelium lining the small blood vessels were also negative for the alu sequence implying they were derived from the mouse vasculature. In addition, there was no cartilage formation observed in sections of different implants and at different time points, as assessed by immunohistochemical analysis using a polyclonal antibody specific for collagen type II (data not shown).

Uses of MPCs

Example 1

Repair of Articular Cartilage

Damaged articular cartilage generated by trauma or by diseases such as osteoarthritis and rheumatoid arthritis usually does not heal. However it is expected that this type of defect could be treated by implanting cultured MPCs of the present invention into the defect. The carrier may be pliable to mould to the shape of the defect and to promote round cell shape which is important for induction of chondrocyte differentiation. A suitable carrier may be constructed of collagen or fibrin. See Caplan et al. in U.S. Pat. No. 5,226,914.

Example 2

Repair of Bone

A combination of MPCs as well as a suitable support can be introduced into a site requiring bone formation. Cultured MPCs contained in calcium phosphate ceramic vehicles may be implanted into the defect site. For appropriate methods and techniques see Caplan et al. in U.S. Pat. No. 5,226,914 and U.S. Pat. No. 5,837,539.

Example 3

Anchoring of Prosthetic Devices

The surface of a prosthetic device can be coated with MPCs prior to implantation. The MSCs can then differentiate into osteogenic cells to thereby speed up the process of bony ingrowth and incorporation of the prosthetic device. See Caplan et al. in U.S. Pat. No. 5,226,914 and U.S. Pat. No. 5,837,539.

Example 4

Gene Therapy

An exogenous nucleic acid that encodes a protein or peptide with therapeutic may be transformed into the enriched population using standard techniques. (see U.S. Pat. No. 5,591,625 by Gerson et al.). The transformed cell population can then be introduced into the body of the patient to treat a disease or condition. For example, can be used to provide a continuous delivery of insulin, or genes encoding Factor VIII which is involved in clotting and therefore may be used in haemophiliacs.

Example 5

Marrow Transplantation

A composition containing purified MPCs can be injected into a patient undergoing marrow transplantation prior to the introduction of the whole marrow. In this way the rate of haemopoiesis may be increased, particularly following radiation or chemotherapy. The composition might also include haemopoietic cells for use in radiotherapy or chemotherapy.

REFERENCES

Alberico et al (1987) *Blood;* 69: 1120.
Allen, T. D.: Haemopoietic microenvironment in vitro: Ultrastructural aspects. In Porter R, Whelan J (eds); "Microenvironments in haemopoietic and lymphoid differentiation." *CIBA Foundation Symposium* 84. London: Pitman Medical, 1981, pp 38.
Allen et al (1990a) *Immunol. Ser.* 49: 1.
Allen et al (1990b) Marrow Biology and Stem Cells. In *Colony Stimulating Factors: Molecular and Cellular Biology*, edited by T. M. Dexter, J. M. Garland and N. G. Testa; New York: Marcel Decker, 1990b, pp 1-38.
Anklesaria et al (1989) *Blood.* 74: 1144.
Anklesaria et al (1987) *Proc. Natl. Acad. Sci. USA.* 84: 7681.
Bennett et al (1991) *Journal of Cell Science.* 99: 131.
Bentley (1982) *Br J Haematol.* 50: 1.
Castro-Malaspina et al (1980) *Blood.* 56: 289.
Castro-Malaspina et al (1981) *Blood.* 57: 781.
Dexter et al (1977) *J Cell Physiol.* 91: 335.
Dexter et al Kroc Foundation Series Vol 18; Alan R. Liss, Inc., New York; p. 57-96, 1984
Fong et al (1997) *BioTechniques,* 23: 1029.
Friedenstein (1976) *International Review of Cytology.* 47: 327.
Friedenstein et al (1970) *Cell Tissue Kinetics.* 3: 393.
Friedenstein et al (1992) *Bone and Mineral.* 18: 199.
Friedenstein (1980) 'Stromal mechanisms of bone marrow: cloning in vitro and retransplantation in vivo'. Immunology of Bone Marrow Transplantation; Ed: S. Thienfelder; Springer-Verlag Berlin; p 19-29, 1980
Gronthos et al (1994) *Blood.* 84: 4164.
Gronthos and Simmons (1995) *Blood.* 85: 929.
Huang and Terstappen (1992) *Nature.* 360: 745.
Keating et al (1982) *Nature.* 298: 280.
Kim et al. (1994) *Science,* 266: 2011.
Knopse et al. (1966) *Blood.* 28: 398.
Knopse et al (1972) *Blood.* 39: 331.
Lichtman (1981) *Experimental Hematology.* 9: 391.
Long (1992) *Exp Hematol.* 20: 288.
MacManus and Weiss (1984) *Blood.* 64: 1036.
McIntyre and Bjornson (1986) *Exp Hematol.* 14: 833.
Miltenyi et al (1990) *Cytometry.* 11: 231.
Owen (1985) *Bone and Mineral Research.* 3: 1.
Owen and Friedenstein (1988) *CIBA Foundation Symposium.* 136: 42.
Perkins and Fleischman (1990) *Blood.* 75: 620.
Piersma et al. (1983) *Br. J. Haematol.* 54: 285.
Rothstein et al (1985) *Blood.* 65: 744
Simmons and Gronthos. (1991) *International Journal of Cell Cloning.* 9: 408 [abstract].
Simmons et al (1994) Advances in Bone Marrow Purging and Processing: Fourth International Symposium. Progress in Clinical Biological Research. 389: 271.
Simmons et al (1987) *Nature.* 328: 429.
Simmons and Torok-Storb (1991a) *Blood.* 78: 55.
Simmons and Torok-Storb (1991b) *Blood.* 78: 2848.
Tavassoli and Friedenstein (1983) *Ann J Haematol.* 15: 195.
Tavassoli and Crosby (1968) *Science.* 161: 54.
Testa et al (1988) Long-term Bone Marrow Damage after Cytotoxic Treatment: Stem Cells and Microenvironment In Hematopoiesis: Long-term Effects of Chemotherapy and Radiation (Hematology/vol 8), eds. Testa, N. G., Gale, R. P., Marcel Dekker, Inc. New York and Basel, 1988, pp 75-92
Van Vlasselaer et al (1994) *Blood.* 84: 753.
Waller et al (1995) *Blood.* 85: 2422.
Weiss (1976) *Anatomical Record.* 186: 161.

---

The invention claimed is:

1. A purified population of STRO-1 positive cells wherein greater than 5% of the STRO-1 positive cells in the population are capable of giving rise to colony forming unit-fibroblasts (CFU-F).

2. The population of STRO-1 positive cells of claim 1, wherein greater than 10% of the STRO-1 positive cells are capable of giving rise to colony forming unit-fibroblasts (CFU-F).

3. The population of STRO-1 positive cells of claim 1, wherein greater than 40% of the STRO-1 positive cells are capable of giving rise to colony forming unit-fibroblasts (CFU-F).

4. The population of STRO-1 positive cells of claim 1, wherein greater than 50% of the STRO-1 positive cells are capable of giving rise to colony forming unit-fibroblasts (CFU-F).

5. The population of STRO-1 positive cells of claim 1, wherein the cells carry at least one additional marker selected from the group of surface markers consisting of THY-1, VCAM-1, STRO-2, and CD146.

6. The population of STRO-1 positive cells of claim 5, wherein the cells carry the marker VCAM-1.

7. The population of STRO-1 positive cells of claim 1, wherein said STRO-1 positive cells are capable of differentiation into at least two committed cell types selected from the group consisting of adipose, areolar, osseous, cartilaginous, elastic, and fibrous connective tissue.

8. The population of STRO-1 positive cells of claim 1, wherein the population is suitable for seeding onto a vehicle for implantation to assist in bone growth.

9. The population of STRO-1 positive cells of claim 1, wherein said STRO-1 positive cells comprise an exogenous nucleic acid that expresses a therapeutic agent transformed into them such that the population of cells may be introduced into the body of a patient to release the therapeutic agent.

10. The population of STRO-1 positive cells of claim 1, wherein the population is used to augment bone marrow transplantation.

11. The population of STRO-1 positive cells of claim 1, wherein the STRO-1 positive cells are negative for at least one marker selected from the group consisting of CBFA-1, collagen type II, PPARγ2, and glycophorin A.

12. A composition comprising a purified population of STRO-1 positive cells wherein greater than 5% of the STRO-1 positive cells are capable of giving rise to colony forming unit-fibroblasts (CFU-F) and haemopoietic cells.

13. The composition of claim 12, wherein the population of STRO-1 positive cells is preadsorbed onto a ceramic vehicle that is precoated with fibronectin and is suitable for implantation to augment bone marrow transplantation.

14. The composition of claim 12, wherein said STRO-1 positive cells comprise an exogenous nucleic acid that expresses a therapeutic agent transformed into them such that the composition may be introduced into the body of a patient to release the therapeutic agent.

* * * * *